US008951168B2

(12) United States Patent
Baudhuin

(10) Patent No.: US 8,951,168 B2
(45) Date of Patent: Feb. 10, 2015

(54) PROGRAMMABLE EXERCISE BICYCLE

(75) Inventor: John R. Baudhuin, Venice, CA (US)

(73) Assignee: Mad Dogg Athletics, Inc., Venice, CA (US)

( * ) Notice: Subject to any disclaimer, the term of this patent is extended or adjusted under 35 U.S.C. 154(b) by 0 days.

(21) Appl. No.: 12/074,864

(22) Filed: Mar. 5, 2008

(65) Prior Publication Data

US 2009/0227429 A1   Sep. 10, 2009

(51) Int. Cl.
| | |
|---|---|
| *A63B 71/00* | (2006.01) |
| *A63B 22/06* | (2006.01) |
| *A63B 71/06* | (2006.01) |
| *A63B 24/00* | (2006.01) |
| *G06F 19/00* | (2011.01) |
| *A63B 21/015* | (2006.01) |
| *A63B 21/22* | (2006.01) |

(52) U.S. Cl.
CPC ......... *A63B 22/0605* (2013.01); *A63B 71/0622* (2013.01); *A63B 24/0062* (2013.01); *G06F 19/3481* (2013.01); *G06F 19/327* (2013.01); *A63B 21/015* (2013.01); *A63B 21/225* (2013.01); *A63B 2022/0658* (2013.01); *A63B 2071/0625* (2013.01); *A63B 2071/0658* (2013.01); *A63B 2225/10* (2013.01); *A63B 2225/15* (2013.01); *A63B 2225/54* (2013.01); *A63B 2230/06* (2013.01); *A63B 2024/0068* (2013.01); *A63B 2220/34* (2013.01); *A63B 2230/062* (2013.01); *G06F 19/328* (2013.01)
USPC .......... 482/57; 482/1; 482/8; 482/51

(58) Field of Classification Search
USPC .................. 482/1–9, 51–53, 57–65
See application file for complete search history.

(56) References Cited

U.S. PATENT DOCUMENTS

| | | | |
|---|---|---|---|
| 562,198 A | 6/1896 | Robinson | |
| 588,166 A | 8/1897 | McCoy | |
| 633,534 A | 9/1899 | Read | |
| 635,082 A | 10/1899 | Stiles | |
| 671,785 A | 4/1901 | Young et al. | |
| 1,336,774 A | 4/1920 | Cooper | |
| 1,507,554 A | 9/1924 | Cooper | |
| 1,636,327 A | 7/1927 | Roe | |
| 3,062,204 A | 11/1962 | Stefano | |
| 3,511,097 A | 5/1970 | Corwin | |
| 3,903,613 A * | 9/1975 | Bisberg | 434/61 |

(Continued)

FOREIGN PATENT DOCUMENTS

| | | |
|---|---|---|
| EP | 0214748 | 3/1987 |
| EP | 1297865 A1 | 4/2003 |

(Continued)

OTHER PUBLICATIONS

Lee W. Young, Written Opinion of the International Searching Authority for PCT/US 09/01327, Apr. 27, 2009.

(Continued)

*Primary Examiner* — Stephen Crow
(74) *Attorney, Agent, or Firm* — Maceiko IP

(57) ABSTRACT

The invention pertains to a stationary exercise bike along with a display that provides instruction to lead a rider through an exercise program. The invention allows a rider to obtain benefits of a group, instructor-led class though the rider's schedule does not permit the rider to participate in the class. The invention also describes a method of exercising with the foregoing bike and display.

26 Claims, 22 Drawing Sheets

(56) References Cited

U.S. PATENT DOCUMENTS

| | | | |
|---|---|---|---|
| D251,747 S | 5/1979 | Valentine et al. | |
| 4,188,030 A | 2/1980 | Hooper | |
| 4,298,893 A | 11/1981 | Holmes | |
| 4,408,613 A * | 10/1983 | Relyea | 600/483 |
| 4,512,566 A | 4/1985 | Bicocchi | |
| 4,512,567 A * | 4/1985 | Phillips | 463/37 |
| D280,117 S | 8/1985 | Collins | |
| D280,118 S | 8/1985 | Collins | |
| 4,556,216 A * | 12/1985 | Pitkanen | 482/131 |
| 4,577,860 A | 3/1986 | Matias | |
| D284,596 S | 7/1986 | McNeil | |
| 4,632,386 A | 12/1986 | Beech | |
| D289,782 S | 5/1987 | Szymski et al. | |
| 4,674,741 A | 6/1987 | Pasierb, Jr. et al. | |
| D291,462 S | 8/1987 | Aalto | |
| D292,304 S | 10/1987 | Ostrom | |
| 4,709,917 A | 12/1987 | Yang | |
| 4,711,447 A | 12/1987 | Mansfield | |
| 4,714,244 A * | 12/1987 | Kolomayets et al. | 482/72 |
| 4,720,789 A * | 1/1988 | Hector et al. | 463/33 |
| 4,768,777 A | 9/1988 | Yang | |
| 4,771,344 A * | 9/1988 | Fallacaro et al. | 386/226 |
| 4,772,069 A | 9/1988 | Szymski | |
| 4,824,102 A | 4/1989 | Lo | |
| 4,867,442 A | 9/1989 | Matthews | |
| 4,880,225 A | 11/1989 | Lucas et al. | |
| 4,902,001 A | 2/1990 | Balbo | |
| 4,915,374 A | 4/1990 | Watkins | |
| 4,919,418 A | 4/1990 | Miller | |
| 4,936,570 A | 6/1990 | Szymski et al. | |
| 5,000,469 A | 3/1991 | Smith | |
| 5,001,632 A | 3/1991 | Hall-Tipping | |
| 5,067,710 A | 11/1991 | Watterson et al. | |
| 5,145,477 A | 9/1992 | Han | |
| 5,149,084 A | 9/1992 | Dalebout et al. | |
| 5,207,621 A | 5/1993 | Koch et al. | |
| 5,232,422 A | 8/1993 | Bishop, Jr. | |
| 5,308,296 A | 5/1994 | Eckstein | |
| 5,335,188 A | 8/1994 | Brisson | |
| 5,336,147 A | 8/1994 | Sweeney, III | |
| 5,362,069 A | 11/1994 | Hall-Tipping | |
| 5,383,826 A | 1/1995 | Michael | |
| 5,407,402 A * | 4/1995 | Brown et al. | 482/4 |
| 5,423,728 A | 6/1995 | Goldberg | |
| 5,489,249 A | 2/1996 | Brewer et al. | |
| 5,512,025 A | 4/1996 | Dalebout et al. | |
| 5,527,239 A * | 6/1996 | Abbondanza | 482/8 |
| 5,584,700 A | 12/1996 | Feldman et al. | |
| 5,643,146 A | 7/1997 | Stark et al. | |
| 5,645,513 A | 7/1997 | Haydocy et al. | |
| 5,667,459 A | 9/1997 | Su | |
| 5,702,323 A | 12/1997 | Poulton | |
| 5,782,639 A | 7/1998 | Beal | |
| 5,785,631 A | 7/1998 | Heidecke | |
| 5,810,696 A * | 9/1998 | Webb | 482/52 |
| 5,830,107 A | 11/1998 | Brigliadoro | |
| 5,836,770 A * | 11/1998 | Powers | 434/247 |
| 5,888,172 A | 3/1999 | Andrus et al. | |
| 5,890,995 A | 4/1999 | Bobick et al. | |
| 5,916,063 A | 6/1999 | Alessandri | |
| 5,947,868 A | 9/1999 | Dugan | |
| 6,004,243 A | 12/1999 | Ewert | |
| 6,027,428 A | 2/2000 | Thomas et al. | |
| 6,059,692 A * | 5/2000 | Hickman | 482/8 |
| 6,152,856 A | 11/2000 | Studor et al. | |
| 6,193,631 B1 * | 2/2001 | Hickman | 482/8 |
| 6,287,239 B1 * | 9/2001 | Hernandez | 482/1 |
| 6,447,424 B1 | 9/2002 | Ashby et al. | |
| 6,450,922 B1 | 9/2002 | Henderson et al. | |
| 6,458,060 B1 | 10/2002 | Watterson et al. | |
| 6,522,255 B1 | 2/2003 | Hsieh | |
| 6,547,702 B1 * | 4/2003 | Heidecke | 482/62 |
| 6,626,799 B2 | 9/2003 | Watterson et al. | |
| 6,672,991 B2 * | 1/2004 | O'Malley | 482/8 |
| 6,701,271 B2 | 3/2004 | Willner et al. | |
| 6,749,537 B1 * | 6/2004 | Hickman | 482/8 |
| 6,793,608 B2 | 9/2004 | Goldberg | |
| 6,808,472 B1 * | 10/2004 | Hickman | 482/8 |
| 6,881,176 B2 * | 4/2005 | Oishi et al. | 482/8 |
| 6,921,351 B1 * | 7/2005 | Hickman et al. | 482/8 |
| 6,932,745 B1 * | 8/2005 | Ellis | 482/52 |
| 7,022,048 B1 * | 4/2006 | Fernandez et al. | 482/8 |
| 7,044,891 B1 * | 5/2006 | Rivera | 482/8 |
| 7,097,588 B2 | 8/2006 | Watterson | |
| 7,166,064 B2 * | 1/2007 | Watterson et al. | 482/54 |
| 7,179,202 B2 * | 2/2007 | Marin et al. | 482/54 |
| 7,357,756 B2 * | 4/2008 | Demas | 482/8 |
| 7,435,202 B2 | 10/2008 | Daly et al. | |
| 7,455,622 B2 * | 11/2008 | Watterson et al. | 482/8 |
| 7,481,744 B2 * | 1/2009 | Reyes et al. | 482/54 |
| 7,510,509 B2 * | 3/2009 | Hickman | 482/8 |
| 7,549,947 B2 * | 6/2009 | Hickman et al. | 482/8 |
| 7,575,536 B1 * | 8/2009 | Hickman | 482/8 |
| 7,601,099 B2 * | 10/2009 | Kang | 482/8 |
| 7,625,315 B2 * | 12/2009 | Hickman | 482/8 |
| 7,637,847 B1 * | 12/2009 | Hickman | 482/8 |
| 7,670,263 B2 * | 3/2010 | Ellis et al. | 482/8 |
| 7,693,584 B2 * | 4/2010 | Pryor et al. | 700/17 |
| 7,713,171 B1 * | 5/2010 | Hickman | 482/4 |
| 7,789,800 B1 | 9/2010 | Watterson et al. | |
| 7,837,595 B2 * | 11/2010 | Rice | 482/4 |
| 7,931,562 B2 * | 4/2011 | Ellis et al. | 482/8 |
| 2002/0173407 A1 * | 11/2002 | Bowman | 482/8 |
| 2003/0171190 A1 * | 9/2003 | Rice | 482/57 |
| 2004/0014566 A1 | 1/2004 | Kao | |
| 2005/0075213 A1 | 4/2005 | Arick | |
| 2006/0046905 A1 | 3/2006 | Doody, Jr. et al. | |
| 2006/0116248 A1 * | 6/2006 | Lofgren et al. | 482/62 |
| 2006/0189439 A1 * | 8/2006 | Baudhuin | 482/8 |
| 2006/0205564 A1 * | 9/2006 | Peterson | 482/8 |
| 2007/0118406 A1 * | 5/2007 | Killin et al. | 705/2 |
| 2007/0170688 A1 | 7/2007 | Watson | |
| 2007/0197345 A1 | 8/2007 | Wallace | |
| 2007/0219059 A1 * | 9/2007 | Schwartz et al. | 482/8 |
| 2007/0225120 A1 | 9/2007 | Schenk | |
| 2007/0281828 A1 * | 12/2007 | Rice | 482/4 |
| 2008/0076637 A1 * | 3/2008 | Gilley et al. | 482/9 |
| 2008/0141135 A1 | 6/2008 | Mason et al. | |
| 2008/0161733 A1 * | 7/2008 | Einav et al. | 601/34 |
| 2008/0194385 A1 * | 8/2008 | Heung | 482/1 |
| 2009/0227429 A1 * | 9/2009 | Baudhuin | 482/57 |
| 2009/0233769 A1 * | 9/2009 | Pryor | 482/8 |
| 2009/0291805 A1 * | 11/2009 | Blum et al. | 482/9 |
| 2009/0312153 A1 * | 12/2009 | Ideno | 482/9 |
| 2010/0075808 A1 * | 3/2010 | Luberski et al. | 482/8 |
| 2010/0255955 A1 * | 10/2010 | Hickman | 482/5 |

FOREIGN PATENT DOCUMENTS

| | | |
|---|---|---|
| TW | I220387 | 8/2004 |
| TW | I290058 | 11/2007 |
| WO | WO9636399 A1 | 11/1996 |
| WO | WO9815112 A3 | 4/1998 |
| WO | WO9900782 A1 | 1/1999 |
| WO | WO 01/70340 A2 | 9/2001 |

OTHER PUBLICATIONS

Spinning Phase I Learning With Johnny G., VHS Video Tape, 1996, PPI Entertainment Group, a division of Peter Pan Industries, Inc., 88 Francis St. Newark, NJ 07105.

Spinning Phase II Riding With Johnny G., VHS Video Tape, 1996, PPI Entertainment Group, a division of Peter Pan Industries Inc., 88 Francis St. Newark, NJ 07105.

PCT International Search Report, Jul. 14, 1995, International Application No. PCT US/95/03878.

Cateye CS 1000 CycloSimulator; http://www.lifestylesport.com/cs1000.htm.

Cateye Gamebike Bicycle Indoor Trainer Accessory; http://www.lifestylesport.com/cateye_gamebike.htm.

Exercise Bike LifeCycle 9100 Upright (Remanufactured); http://www.bigfitness.com/bigfit/liffitbrlif9.html.

Kurt Kinetic Trainers; http://www.lifestylesport.com/kurt_kinetic_trainers.htm.

(56) References Cited

OTHER PUBLICATIONS

LCD Technology Life Fitness; http://us.commercial.lifefitness.com/content.cfm/lcd.

Life Cycle Entertainment; http://www.fitego.com/lifcycexrem.html.

LifeFitness Lifecycle 9500 HRT Remanufactured; http://www.egymequipment.com/egymequipment-store/lif95hrtupre.html.

Sheldon Brown's Bicycle Glossary; www.sheldonbrown.com/glossary.html.

PCT, Written Opinion of the International Searching Authority, May 12, 2006, International Application No. PCT/US2006/003702, 3 pages.

PCT, International Search Report, May 12, 2006, International Application No. PCT/US2006/003702, 1 page.

PCT, International Preliminary Report on Patentability, Aug. 7, 2007, International Application No. PCT/US2006/003702, 4 pages.

PCT, International Preliminary Report on Patentability, Mar. 18, 2010, International Application No. PCT/US2009/01327, 6 pages.

PCT, International Preliminary Report on Patentability (Corrected), Mar. 18, 2010, International Application No. PCT/US2009/01327, 6 pages.

EPO, Supplementary European Search Report, Jan. 13, 2011, Application No. EP 06734224, 7 pages.

* cited by examiner

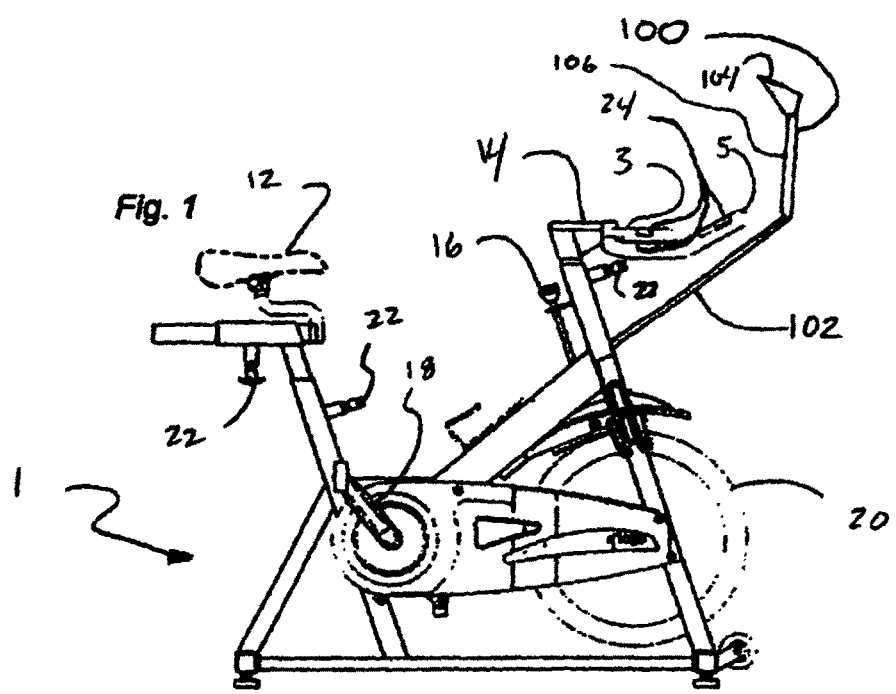

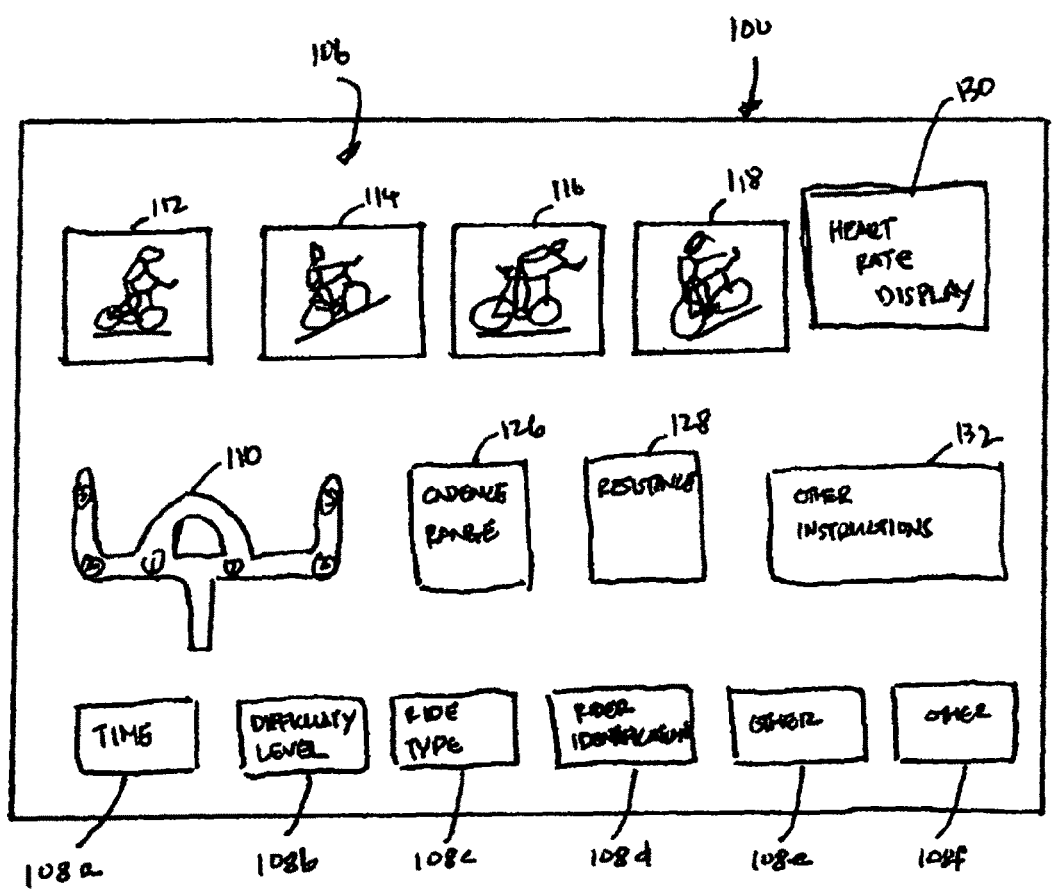

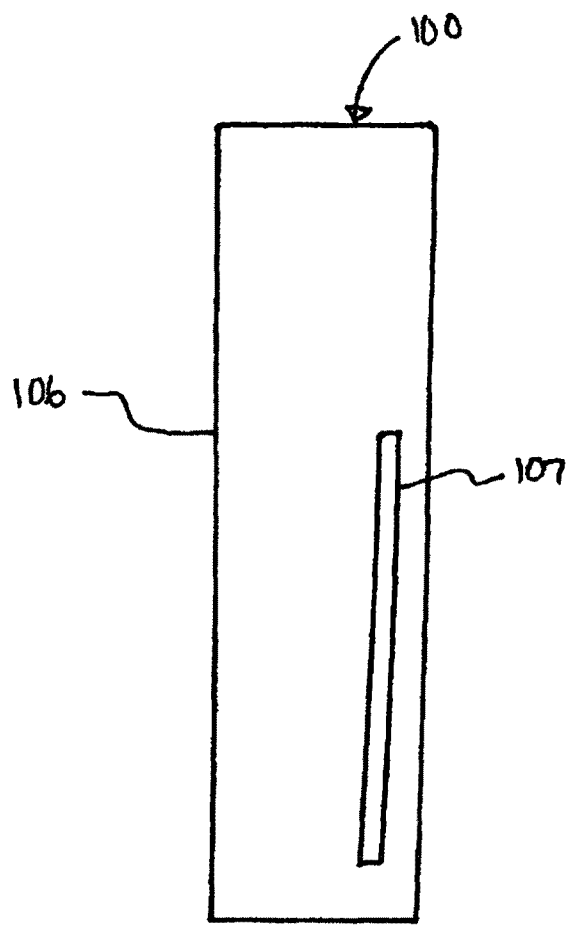

PROGRAMMABLE EXERCISE BICYCLE

FIELD OF THE INVENTION

The invention generally relates to exercise devices and programs. More specifically, the invention relates to providing instructions to an exercise participant to lead the participant through an exercise program. The invention also relates to the use of a stationary exercise bike that may be programmed by the participant.

An embodiment of the invention relates to the use of an indoor exercise bike along with instructions similar to those provided by an instructor during an indoor exercise bike program. In this embodiment, the participant is instructed to assume different hand and riding positions throughout the program.

BACKGROUND OF THE INVENTION

In recent years, instructor-led exercise classes using stationary exercise bikes have become increasingly popular. Since the advent of the indoor cycling exercise program, various indoor cycling classes have come into existence. In such classes, the instructor typically leads a class of participants by instructing them to assume different riding positions, such as sitting and standing in combination with different hand positions on the handlebars. The instructor also may instruct participants to vary their pedaling cadence to simulate sprinting or other riding conditions. The bikes used in these classes typically have a resistance device to vary how difficult it is to pedal, and the instructor may also instruct participants to vary the resistance to simulate different riding conditions such as hill climbing.

Many participants seek out instructor-led classes for the encouragement and expertise that an instructor may provide during the exercise program, or the camaraderie between participants. However, instructor-led classes generally adhere to a predetermined time schedule. This presents a problem to participants that cannot attend predetermined classes because of their jobs or other scheduling conflicts.

Health clubs typically have different types of stationary exercise bikes available on their floors for individuals to ride. However, these bikes typically do not have the open geometry, adjustability or other characteristics that allow an individual to experience an exercise program such as provided by indoor cycling programs. In other words, the bikes themselves are inadequate.

Certain health clubs may have indoor cycling bikes available on their floor to ride by individuals who are not participating in an instructor-led class. But without an instructor, the individual may not receive the proper instruction or guidance essential to properly adjusting the bike to ride, or essential to simulating the different riding positions and/or resistances and/or pedal cadences that an instructor typically provides during a class. Indeed, instructors such as certified SPINNING® instructors receive significant and ongoing training in order to lead classes. Accordingly, the individual that simply pedals a stationary exercise bike on a health club floor will generally not achieve the benefits of an instructor-led class. Furthermore, the lack of an instructor may increase the danger of injury if the individual is not riding the bike correctly or the bike is not properly adjusted. This may be especially so where the bike is in a direct drive or fixed gear configuration.

Accordingly, a need exists for a stationary exercise bike for use by an individual who is not participating in an instructor-led class, wherein the bike itself allows different riding positions and conditions, and also provides instruction to the individual so that the individual may receive benefits typically received during an instructor-led class. There also exists a need for the stationary bike to take the rider's ability, past exercise history and/or heart rate into account.

Previously, videos of an instructor providing instruction for an indoor cycling bike class have been available for an individual to watch as he or she rides an indoor cycling bike. However, such videos require a separate VCR and monitor to play the video. Besides requiring additional equipment, the space required may also not be available. For example, space on a health club floor is generally considered to be at a premium.

U.S. Pat. No. 6,287,239 to Hernandez purports to disclose the use of an indoor cycling bike and a display screen with a cartridge that plays music and provides directions to the rider. However, the disclosure of the '239 patent is very limited and the bike pictured in the patent would not enable a participant to simulate different riding positions and conditions, or experience an indoor exercise bike program. The '239 patent also does not disclose how the rider's ability, past exercise history and/or heart rate may be taken into account when providing instructions to the participant, or how the rider may program the exercise parameters himself or herself. The '239 patent also does not address adjusting the bike to properly set it up.

The present invention solves the above-identified and other needs.

SUMMARY OF THE INVENTION

In a first aspect of the invention, a stationary exercise bike for indoor cycling is used along with a display that provides instruction to lead a rider through an exercise ride.

In another aspect of the invention, a rider may program the bike to customize the exercise routine.

In another aspect of the invention, a stationary exercise bike that takes into account the rider's ability, cadence, distance, time, past exercise history and/or heart rate is described.

In another aspect of the invention, a method of exercising with the foregoing bike and display is described.

In another aspect of the invention, a display module that may be attached to existing exercise devices is disclosed.

BRIEF DESCRIPTION OF THE DRAWINGS

FIG. 1 shows a stationary exercise bike with a display screen.

FIG. 2A shows a front view of a display featuring the display screen.

FIG. 3 shows a side view of a display.

DETAILED DESCRIPTION OF THE PREFERRED EMBODIMENTS

Figure 2B:
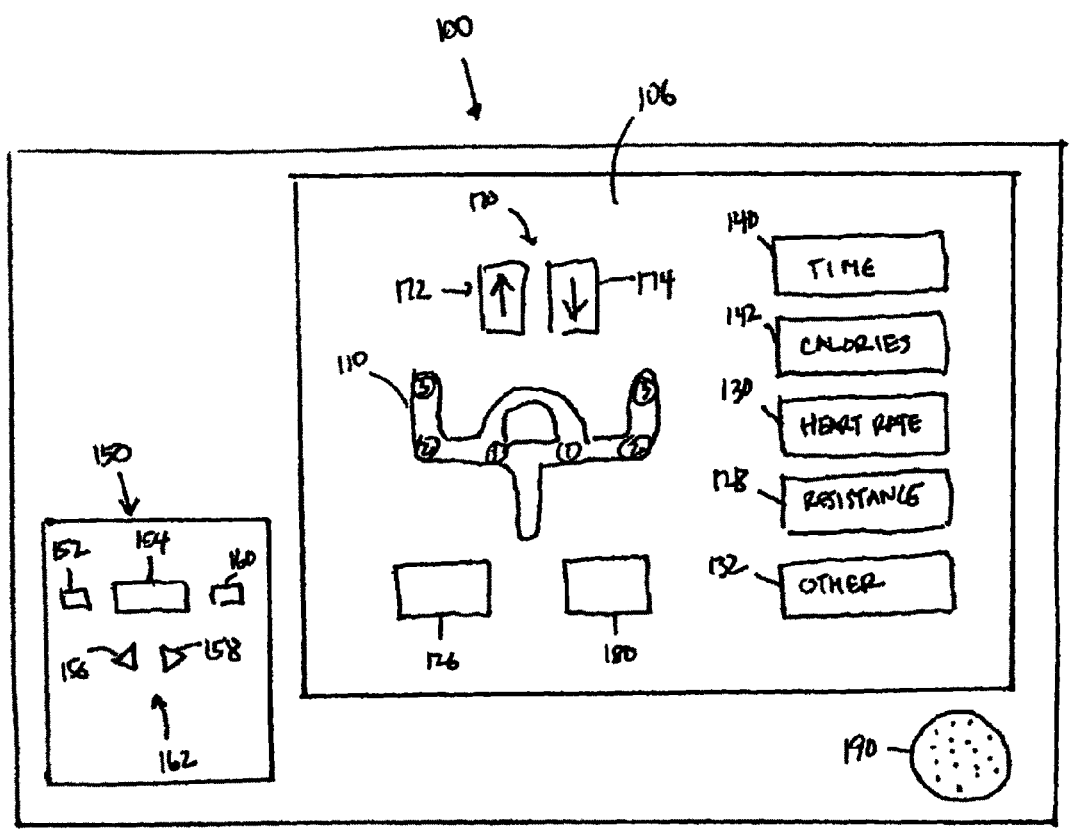
FIG. 2B shows an alternate front view of a display.

Generally, the invention serves to provide instructions to a rider that leads the rider through an exercise program. It is preferred that the instruction be similar to that provided in instructor-led classes so that the rider obtains the benefits of such classes despite the fact that the rider's schedule conflicts with pre-scheduled instructor-led classes.

FIG. 1 shows a stationary exercise bike 10 along with a display screen 100. The display screen includes a computer or other device to store and/or provide instructions. The bike 10 shown is an indoor cycling bike that is adjustable and has an open geometry that allows a rider to simulate different riding positions and conditions. Bike 10 preferably includes adjustable seat assembly 12, adjustable handlebar 14 having multiple hand position, variable resistance mechanism 16, pedal assembly 18 and flywheel 20 which is coupled to pedal assembly 18 in a direct drive (fixed gear) and/or non direct drive e.g., freewheeling configuration. U.S. Pat. Nos. 6,468,185 and 6,793,608 are hereby incorporated by reference herein in their entireties. A clutching mechanism may also be included which may be preferred where bike 10 is in a fixed gear configuration. U.S. Pat. No. 5,961,424 is hereby incorporated by reference herein.

Various pop-pins (or other suitable mechanism) 22 may be used to effect up/down and fore/aft adjustment of seat 12, up/down adjustment of handlebar 14 and up/down adjustment of display 100. It is preferred that the seat and handlebar be adjusted to safely accommodate different riding positions such as sitting and standing, as well as different hand positions. Handlebar 14 may include one or more sensors 24 to measure the rider's pulse and heart rate. This information may be sent to the computer (discussed below). The computer may also receive heart rate signals from a monitor/transmitter worn by the rider.

Display 100 may be attached to bike 10 by a bracket 102. Display 100 includes screen 106 on which various information is input and/or displayed. Brackets different than that shown may be used, and bracket 102 may attach to bike 10 at different locations. It is preferred that display 100 not interfere with the rider's ability to grasp handlebar 3 at different locations so that the rider may assume different riding positions. For example, when the rider is standing and his or her hands are near the forward end 5 of handlebar 3, it is preferred that display 100 not interfere with this position. It is also preferred that display 100 be located so that the rider does not excessively sweat on it. The display 100 preferably comprises an outer shell of plastic or other material that is resistant to sweat.

Display 100 may also be fitted with a hood 104 that may extend around the top of display 100 to provide better contrast between the ambient light and the information illuminated on display 100. Hood 104 may also extend around the sides and bottom of display. Hood 104 may also help prevent excessive sweat from dripping on display 100. Screen 106 may comprise a computer screen, LED or other type of visual display. In a preferred embodiment, screen 106 may comprise a touch screen with suitable sensors and software. Screen 106 may receive and/or display numerical, textual, or graphical information.

Display 100 is now further discussed with reference to FIGS. 2A, 2B, and 3. It should be noted that the exact visual components displayed on screen 106 of the display 100 may vary from that shown in FIG. 2A or 2B or be a combination thereof. A computer or other storage device (not shown) is preferably contained within display 100. However, the computer or other storage device may be remotely located. The computer preferably stores riding instructions that are conveyed to the rider through display 100. The computer may also receive instructions and/or data from the rider through an input device 150 contained within the display 100 so that the instructions provided during the ride may be customized per the rider's specifications.

The input device 150 may be accessed through a menu button 152 and viewed through the menu screen 154. Each time the menu button 152 is pressed, one of a plurality of parameters is accessed. Once a particular parameter is accessed, a pair of directional arrows 162 may be used to scroll through the various possibilities. The left arrow 156 generally changes the value lower while the right arrow 158 generally changes the value higher. The rider may then select a particular value or parameter by pushing the select button 160.

The following is a list of the various parameters which may be accessed and set through input device 150, but is not intended to be exhaustive.

Time duration for the workout. Generally, a default time for the workout may be set. However, the rider may choose to shorten or lengthen the workout time as they desire. Once the workout starts, the overall time and/or time remaining may be displayed on the time display 140 that is located in the display screen 106.

The calories to be burned during the workout. The number of calories the rider wishes to burn may be selected by the rider. As the workout begins, the number of calories burned may be displayed on the calorie display 142 that is located in the display screen 106.

Level of intensity. Rather than selecting the number of calories burned, the rider may choose to simply select an intensity level and allow the computer to generate an appropriate workout routine. The higher the level of intensity chosen, the computer may generate a workout with greater resistance, a higher level of cadence, and/or instruct the rider to assume riding positions that are generally considered more difficult.

Type of ride, e.g., hill, flat, random or other types of pre-programmed workout. Depending on the type of workout, the display 100 may provide different types of instructions. For example, a hill ride might involve more sitting than standing.

Weight of the rider. The rider may enter this information to determine the effect on calories burned or other parameters.

Maximum heart rate. A maximum heart rate may be calculated using age-predicted charts, e.g., by subtracting the rider's age from 220 for male riders and subtracting from 226 for female riders. However, other medical based algorithms may be used to calculate maximum heart rate and may be programmed into the bike. A more accurate rate may be determined by undergoing a maximum heart rate test. The maximum heart rate preferably enables the computer to control the workout by decreasing or increasing the level of intensity to achieve a desired heart rate level.

Identification Number or Other Device. The rider may be assigned to an identification number, thereby allowing the computer to access and store certain information about a particular rider. Once assigned to a particular identification number, the rider may log in with the identification number to identify themselves and store various workouts in the computer. The computer may store the workout parameters and rider's fitness progress based on the duration of the workout, power exerted during prior workouts, calories burned or other parameters.

As an alternative to a rider punching in an identification number, a radio frequency identification device (RFID) may be used. For example, the rider may wear an RFID band around his or her wrist and use that to access the computer.

In this manner, the computer may automatically devise a set of instructions that push the rider to achieve a new fitness level by generating progressively more difficult workout routines. The computer may also have safeguards to prevent the rider from being advanced to quickly. For example, the computer may generate more difficult workouts only after a particular rider has had at least some number of workouts during a certain time period. The rider may also save workout routines under their identification number for easy access in the future.

As an alternative to the computer discussed above, display 100 may include a device to receive a CD-ROM, DVD, VHS tape or other storage medium that contains or receives riding instructions. As shown in FIG. 3, display 100 may include opening 107 to receive such a storage media.

Alternatively, display 100 may include a device enabling connection of the computer with the internet or some other computer network. In this embodiment, the computer may send and receive data over the internet.

The inputting of information is now more specifically described. By way of example, the first time a rider presses the menu button 152, the menu screen 154 may flash "ID" or some other appropriate message to indicate the rider should input their identification number. The directional arrows 162 may be used to scroll through the various possibilities from "None" to a numerical value ranging from 1 to however many unique users may be supported by the computer's memory. It is noted that today's storage media have large memory capacities providing for the storage of information for many riders. Alternatively, the rider may punch in his or her ID number. The computer may also request a password be entered. It is also contemplated that other forms of identification may be used such as a Smart Card, memory key, or other similar device.

If "none" is selected using the select button 160, the menu screen may ask the rider if they would like to be assigned to an identification number. The rider may select the next available number and provide password information. The rider can then move through and select a value for each of the parameters discussed above in a similar fashion.

At the end of each workout routine, if the workout was assigned to an identification number, the menu screen 154 may ask the rider if they wish to record the workout as part of their history file. Then, if the workout routine was a new routine that was not previously saved, the menu screen 154 will ask the user if they wish to save the workout routine. If the answer is yes, then the rider may name the workout routine.

Once again, the directional arrows 162 and the select button 160 may be used to scroll through and select letters and numbers to name the workout routine. In this manner ride profiles may be stored in the computer so that they may be recalled at a later time. For example, when the rider comes to the rider identification screen, a separate instructions display 132 that is located in the display screen 106 may list the ride profiles previously stored by the rider and ask the rider to choose one.

The computer may store and generate any number of work out routines including pre-programmed ones, routines saved by the user, and new routines based upon the rider's specific parameters.

Screen 106 preferably includes icons and screens that instruct the rider through the workout with different hand positions, riding positions, and varying pedaling speeds. Hand positions are shown to the rider with a handlebar icon 110 which may include first, second and third hand positions (110(1), 110(2) and 110(3)) that light up at different times signifying that the rider should change his or her hand positions. Hand positions 110(1), 110(2) and 110(3) preferably illuminate at appropriate times.

The rider's appropriate position may be shown to the rider through a pair of arrow icons 170 comprised of an up arrow icon 172 and a down arrow icon 174. When the workout requires the rider to be in the standing position, the up arrow icon 172 may be illuminated. When the workout requires the rider to be in the sitting position, the down arrow icon 174 may be illuminated. Both the up arrow icon 172 and the down arrow icon 174 may be illuminated when the rider is to alternate between standing and sitting.

Screen 106 may also include a target cadence display 180 that provides the rider with a certain range of desired cadence. The cadence range displayed may change as the riding position change. For example, a higher cadence range may be specified when the rider is seated and a lower cadence range may be specified when the rider is standing and climbing.

The computer in display 100 may be coupled to the pedal assembly 18 so that the computer may measure the rider's actual cadence. If the rider's cadence is within the desired range being displayed on a target cadence display 180 located in the display screen 106, a cadence screen 126 that is also located on the display screen 106 may illuminate in a certain way, e.g., non-flashing. If the rider's cadence is not within the desired range shown on the target cadence display 180, the rider's cadence screen showing the rider's actual cadence may illuminate in a flashing manner which preferably attracts the rider's attention so that the rider may adjust his or her cadence to bring it within the desired range.

Alternatively, screen 106 preferably includes a series of icons that instruct the rider through the ride with different combination of hand positions, riding positions, e.g., sitting or standing, and different riding conditions, e.g., flats, hills, climbing, sprinting, etc. The icons may be associated with a particular type of indoor cycling, or may be self-explanatory.

For example as shown in FIG. 2, the icons may comprise a graphic that illustrates a rider on a bike. Riding position icons may include seated flat 112, seated climbing 114, standing flat 116, and standing climbing 118. Each of these riding positions icons may light up at different times throughout the ride to signify that the rider should change positions. In this manner, the rider need not memorize riding position symbols that may be associated with a particular type of indoor cycling. As another alternative, or in addition to the foregoing, word text, such as "sit" or "stand", may illuminate on screen 106 to help instruct the rider's position.

Screen 106 may also include a resistance display 128 that provides the rider with an instructed resistance level. The resistance displayed may vary when different riding position icons are illuminated. For example, the resistance may be increased when the standing climbing icon 118 is illuminated. (Generally, in this situation, hand position 3 (110(3)) will be illuminated.) The rider may adjust the resistance device according to the resistance displayed. When the resistance value on display 128 changes, it may flash to attract the rider's attention so that the rider may change the resistance at the appropriate time. Alternatively, the resistance may be computer controlled and change automatically.

The cadence may be increased while the resistance remains constant to effect cadence building. The resistance may be increased while the cadence remains constant to effect resistance loading. The foregoing may be achieved by varying the numbers displayed on the target cadence display 180 and/or the resistance display 128.

Screen 106 also preferably includes a heart rate display 130 which displays the rider's heart rate as picked up by the sensors 24 on the handlebar 14 or monitor/transmitter worn by the rider. The location of sensors 24 in handlebar 14 preferably correspond to hand positions 1, 2 and 3 on handlebar icon 110. The heart rate may affect the instructions provided to the rider. For instance, if too high of a heart rate is recorded for too long, the rider may be instructed to slow the pedaling cadence through the target cadence display 180 and/or to assume a different riding position that requires less exertion.

Additionally, the sensors 24 may be coupled with lights that turn on to signal to the rider the appropriate position for the rider's hand.

In addition, the display 100 may also include a speaker 190. The speaker may be connected to a computer, a stereo, a video monitor, or other type of multi media device. The speaker 190 may be used to enable riders to hear audible beeps indicating a change is position is needed. The speaker 190 may also enable the rider to listen to instructions or information as well as various entertainment media such as music.

Figure 4:
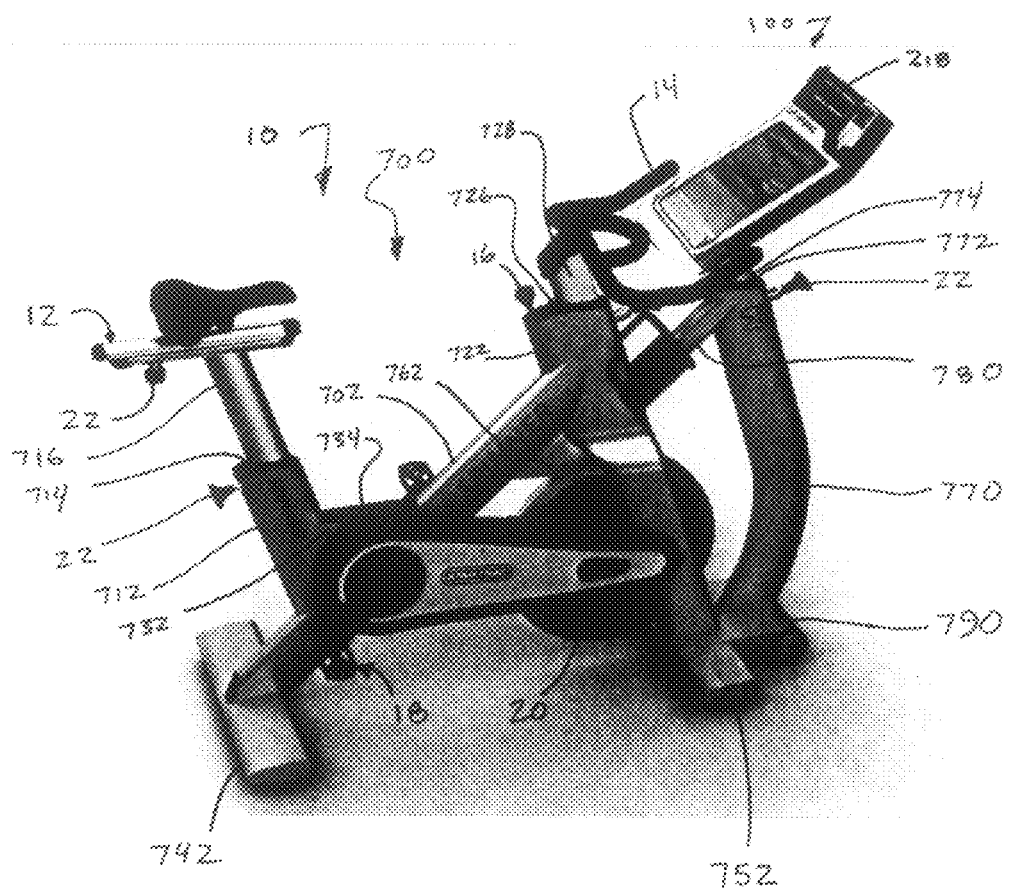
FIG. 4 shows an alternate embodiment of a programmable stationary exercise bike.

An alternate embodiment of bike 10 having frame 700 is now described with reference to FIG. 4. As shown, frame 700 may include down tube or diagonal member 702, rear member or seat socket 712, front member or handlebar socket 722, rear shield or member 732, rear support 742, front support 752, forks 729 and front shield or member 762. Frame 700 need not include all of the foregoing elements.

It is preferred that the materials used to construct the elements of frame 700 are suitably strong so that bike 10 exhibits a rigid feel that may withstand a rider's sitting and standing, and rocking from side to side. An example material is extruded aluminum, though other materials may be used. It is also preferred that the elements are attached together through welds or other suitable means to provide rigidity. It is also preferred that rear support 742 and front support 752 are sufficiently wide so that bike 10 is stable even while the rider rides in a side to side rocking fashion. The supports 742, 752 need not be of the same width.

It should be noted that the foregoing elements may comprise square, rectangular, elliptical and/or other cross-sectionally shaped members. As one example the foregoing element may comprise extruded aluminum pieces that attached together to provide an aesthetically pleasing and smooth contiguous appearance. As an alternative, after these members are attached, they may be covered by a cover or shroud for an improved appearance. In this case the cover may also provide rigidity to frame 700. The cover may also protect the welds or other attachment means between the frame components from the rider's sweat.

Diagonal member 702 may extend upward from rear support 742 to front member 722, and may include a hole to accommodate a crank set of pedal assembly 18. Pedal assembly 18 may also be attached to or located near diagonal member 702 by other suitable means.

Rear member 712 may be attached to down tube 712, and preferably includes a socket 714 to receive seat support 716. Seat socket 714 may include an insert that fits inside rear member 712 and that has a bore to accommodate seat support 716. Socket 714 may comprise plastic. Pop pin 22 may be disengaged to allow seat support 716 to be adjustable up or down. Rear shield member 732 may extend between seat socket 712 and diagonal member 702 and be attached thereto to provide rigidity to frame 700. Rear shield 732 may also serve to protect moving parts such as pedal assembly 18 from the rider's sweat. Rear shield 732 may also include a non-slip cover 734 that may provide safety if the rider steps on rear shield 732.

Front member 722 may be attached to diagonal member 702. Front member 722 may include a bore 724 through which the variable resistance device 16 may extend. Front member 722 may also include handlebar socket 726 to receive handlebar support 728. Handlebar socket 726 may include an insert that fits inside front member 722 and that has a bore to accommodate handlebar support 728. Socket 726 may comprise plastic. Pop pin 22 may be disengaged to allow handlebar support 728 to adjust up or down. Forks 729 may extend from front member 722 to front support 752.

Front shield or member 762 may extend between diagonal member 702 and front member 722 and be attached thereto. Front shield 762 may provide rigidity to frame 700, and may also prevent the rider's sweat from contacting moving parts such as flywheel 20.

Flywheel 20 may be mounted to brackets (not shown) that extend from forks 729. Flywheel 20 is preferably coupled to pedal assembly 18 as described previously.

Display stand or bracket 770 may be included in or attached to frame 700 by upper member 780 and lower member 790. Display stand 770 may comprise extruded aluminum and have an appearance similar to the components of frame 700. Alternatively, a cover on frame 700 may extend over bracket 770 and upper and lower members 780, 790. A power cord and transformer may be included within display stand 770 so that display 100 may receive electrical power from a standard electrical outlet.

Display stand 770 preferably includes socket 772 to receive display support 774 on which display 100 may be attached. Socket 772 may include an insert that fits inside display stand 770 and that has a bore to accommodate support 774. Socket 772 may comprise plastic. Pop pin 22 may be disengaged to adjust display 100 up or down. The connection between display 100 and display support 774 may include a hinge or other suitable mechanism so that display 100 may be rotated relative to display support 774.

Display stand 770 is preferably configured to position display 100 at a location so that display 100 may be easily viewed by the rider. To this end, it is preferred that display 100 not interfere with the rider's hands when positioned at different locations on handlebar 14. It is preferred that a suitable space exist between display 100 and handlebar 14.

An alternate embodiment of display 200, which may attach to display support 774, is now described with reference to FIG. 5. As shown, display 200 may include frame 210 and screen 250, and both of these components are preferably constructed of materials that withstand a rider's sweat. As discussed below, it is preferred that display 200 allows the rider to choose and/or program a variety of exercises. Display 200 also preferably displays information to optimize the rider's exercise as well as safety.

Frame 210 may include a jack 212 for headphones or other devices, location or indentation 218 to place a logo or other advertising material and cavity 220. Cavity 220 may serve to physically hold an item such as an iPod™ or other device that may play music or provide audible instruction or other sounds. Alternatively, cavity 220 may serve as a docking station so that, for example, a rider may dock his or her iPod™ or other device in cavity 220. As discussed in detail later, the iPod™ or other device may then provide video and/or audible content to display 200. Display 200 may also include a speaker 222 to provide audio content such as beeps, spoken instructions, music or other audio content.

Screen 250 may include buttons or touch screen technology with appropriate sensors and software for the rider to enter information. Screen 250 may display a series of screens having different subject matters. For example, screen 250 may display the screen shown in FIG. 5, which is a sample setup screen 270 wherein the rider may input information about himself or herself and the intended ride. This screen is discussed in more detail below.

Figure 6:
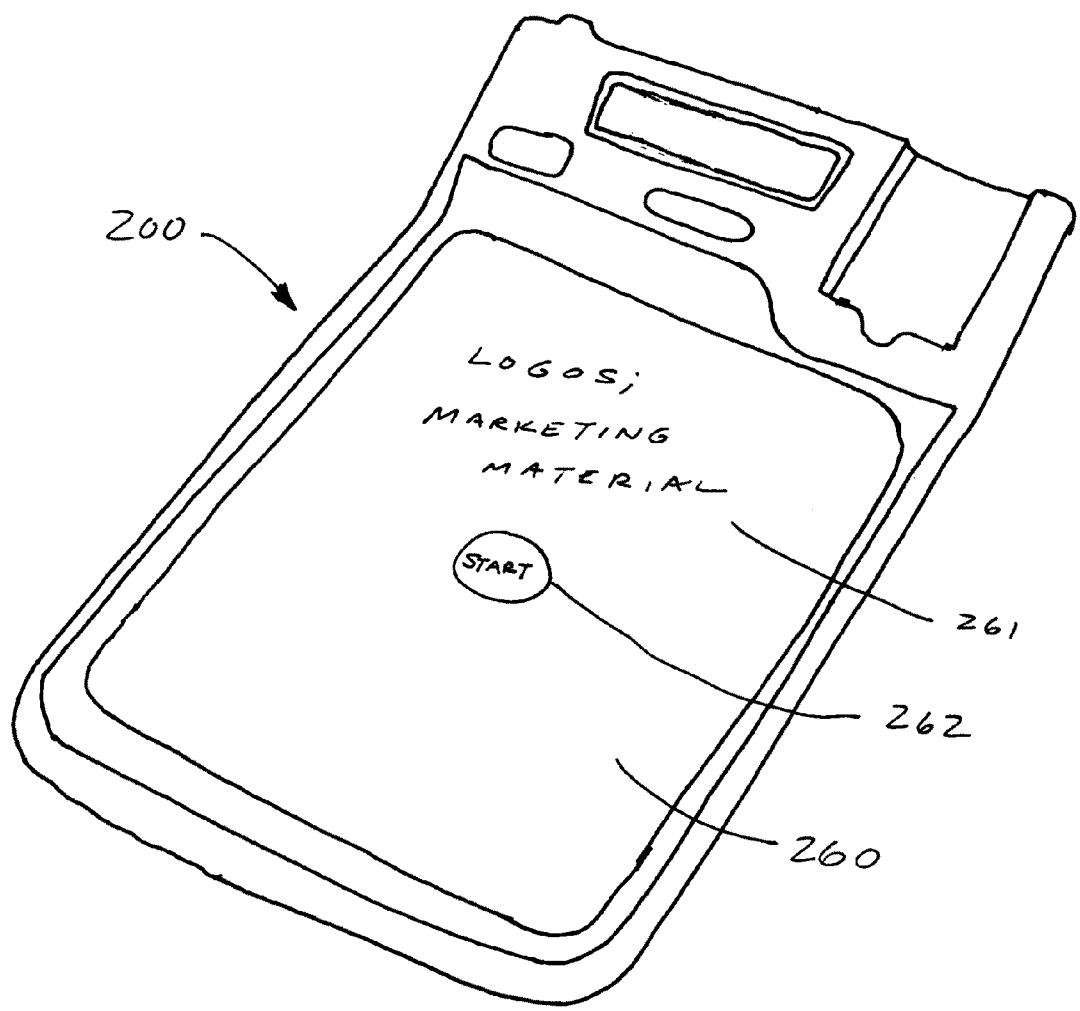
FIG. 6 shows a greeting screen of a display.

Initially, however, display 200 may display an initial or greeting screen 260 such as that shown in FIG. 6. Greeting screen 260 may include logos or other marketing material 261, and may also include a start button 262. Upon the rider's pressing start button 262, an appropriate safety warning, terms of use for the bike and/or disclaimer may appear on screen 250. To proceed further, it is preferred that the rider be required to hit an "I accept" or other acknowledgment.

Figure 7:
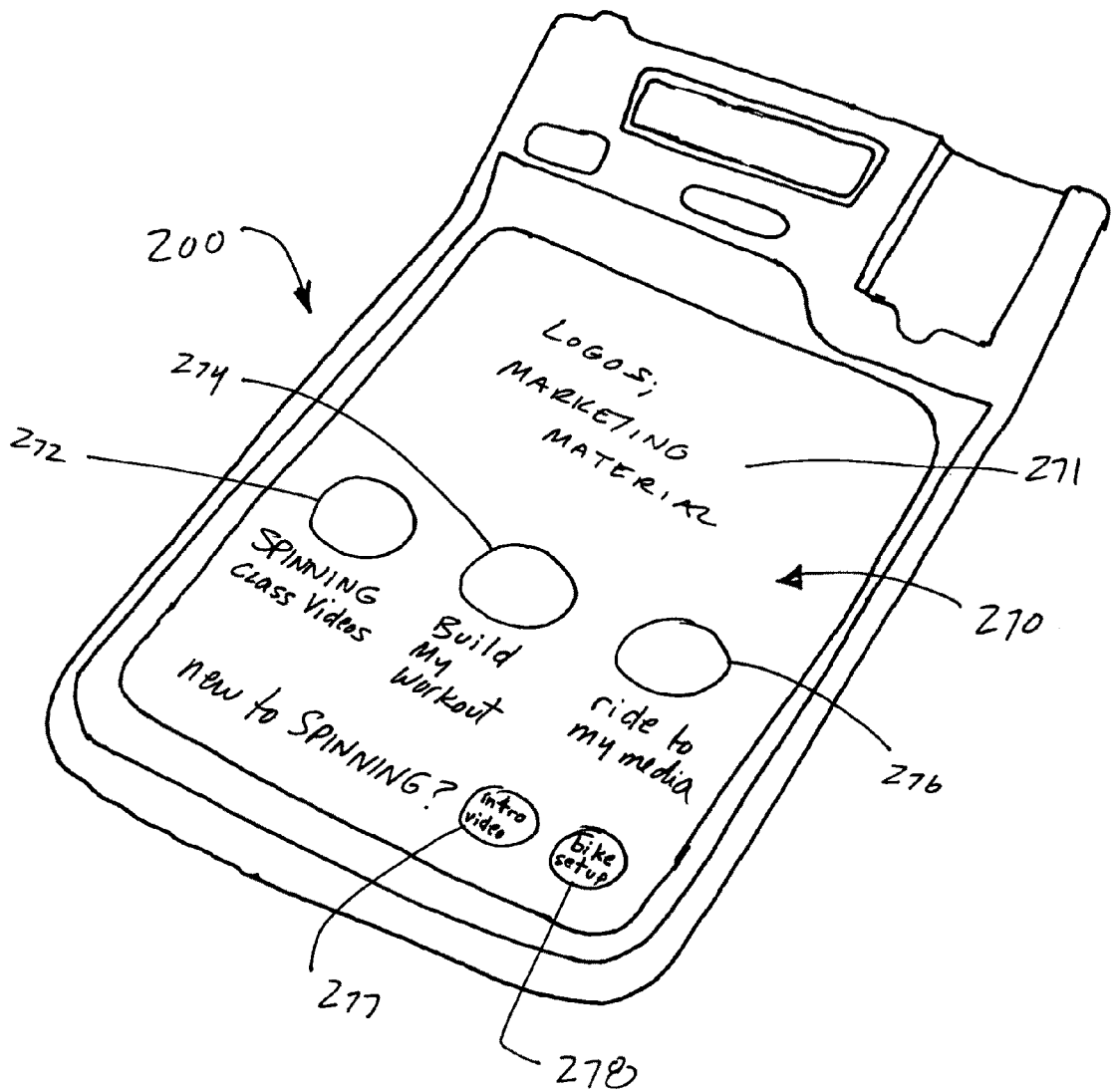
FIG. 7 shows a screen of a display.

Once the rider makes the appropriate acknowledgement, display 200 may display screen 270 as shown in FIG. 7. Screen 270 may include logos or other marketing material 271. Screen 270 may also provide the user with several options on how to exercise or to otherwise proceed. As shown, the user may choose the SPINNING class videos option 272, the build my own workout option 274 or the ride to my media option 276. These options are discussed in more detail below.

Welcome screen 270 may also include other options that may be geared to the newer rider such as introductory video 277. Video 277 may provide general information on how to use the bike, safety and other information. To this end, after video 277 is chosen, the content displayed by screen 250 may change to screen 280, a portion of which may comprise video screen 282 in which the introductory video is shown. This introductory video 277 may comprise a tutorial on riding the bike, such as by providing instructions on basic riding positions. The introductory video may be accompanied by audible instruction through speaker 222, the volume of which may be increased or decreased by buttons 284a and 284b. Volume indicator 286 may show the volume level. Volume may be decreased to mute. Screen 280 may include a stop/pause button 280 which will allow the rider to stop or pause the video.

After the introductory video is over, the rider preferably has the option to go back to screen 270 to select one of the exercise options mentioned above. To this end, screen 280 may include back button 288.

Figure 8:
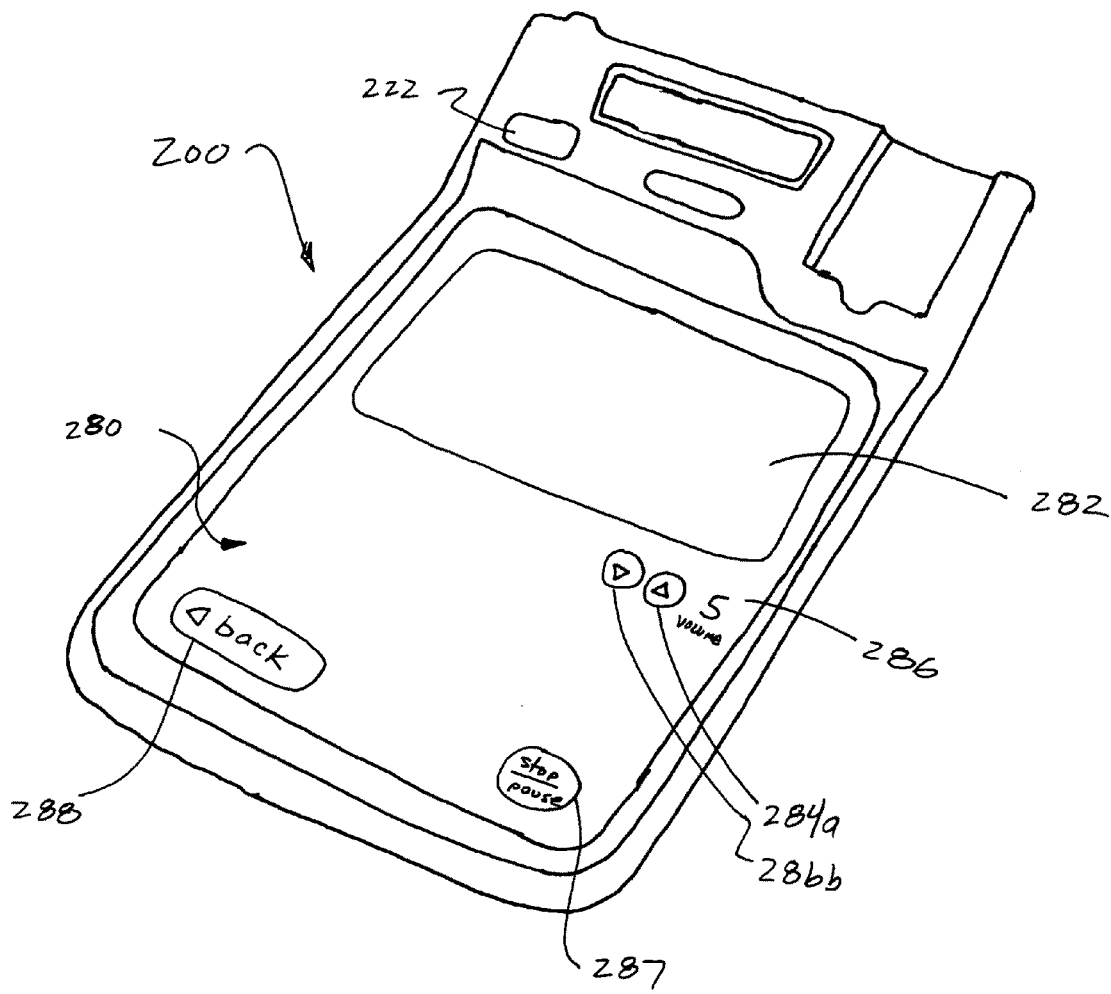
FIG. 8 shows a screen of a display.

Once back at screen 270, the rider may choose one of the exercise options or may choose the bike setup 278 option. Once the bike setup option 278 is chosen, the screen may again assume the configuration of FIG. 8, and video screen 282 may provide instructions to the rider on how to set up the bike for the exercise, e.g., appropriate adjustment of the handlebars and seat.

For example, video screen 282 may display a video, pictures or graphics that provide instruction for the proper positioning on the bike for control and safety purposes. The bike setup option 278 may aid in proper seat adjustment by showing the proper knee bend so that the rider may adjust seat height. If a video, the rider may pause the video until he or she has properly adjusted the seat. Once this is accomplished, the rider may advance the content on screen 282 to show how the rider's knee cap should be above the pedal in the forward most position to adjust the fore/aft position of the seat. The rider may then proceed to another screen showing a graphic or picture on screen 250 about handlebar height. Volume may be controlled as described above.

Once the bike setup 278 screens have been complete, the rider may hit back button 288 and return to screen 270 to choose an exercise program. The different exercise programs are now discussed in more detail.

Figure 10:
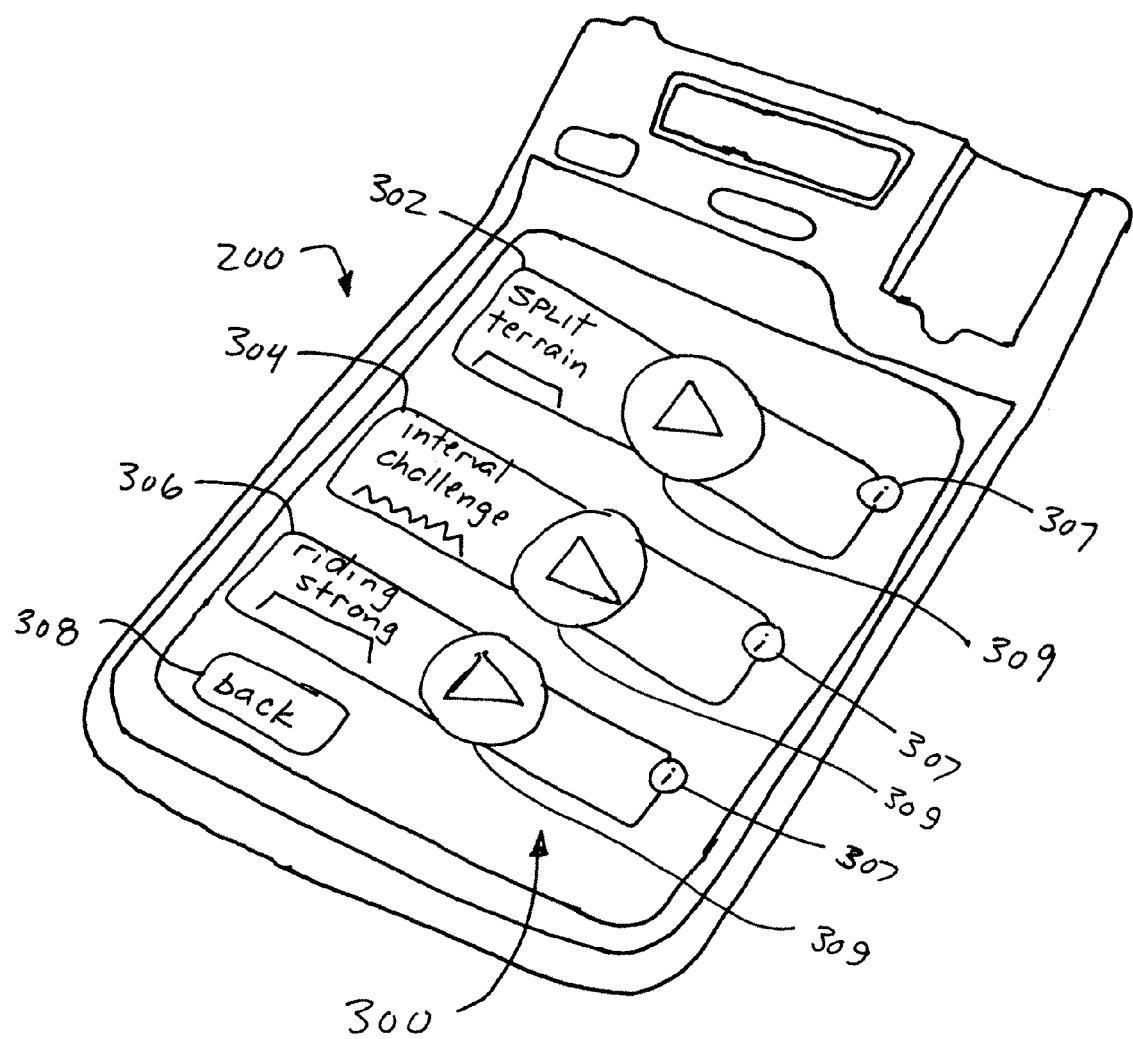
FIG. 10 shows a screen of a display.

If the rider chooses the build my workout option 274, display 200 may display the screen 300 of FIG. 10. As shown, screen 300 may display three different types of workouts that the rider may choose: split terrain 302, interval challenge 304 and riding strong or strength 306. The user may hit the information button 307 on any of these options and screen 300 may display a textual description of what that exercise entails.

For example, pressing information button 307 for interval 304 may result in the following text appearing on screen 300: "Speed, tempo, timing and rhythm—requires substantial fitness base. Exercise intensity: 65% to 75% of maximum heart rate." If this appeals to the rider, the rider may then proceed to build his or her interval workout as discussed below. If not, the rider may push the information button 307 associated with the other exercises displayed to obtain a preview of what the other exercise routines entail.

It should be noted that the three exercises identified above are only examples and the present invention contemplates various other exercise routines. In one embodiment, screen 300 may preferably scroll up or down so that other exercise routines are displayed. Other workout routines associated with SPINNING may be used. For example, recovery, endurance, strength, interval and race day workout routines may be used. The riding positions, hand positions, segments, cadences and other information associated with these workout routines may be provided by the bike of the current invention. To that end, the Manual for the SPINNER Instructor Training Program is hereby incorporated by reference in its entirety.

Figure 5:
FIG. 5 shown an alternate display.

To build the workout, the rider may press the arrow button 309 of the chosen exercise routine which preferably provides the rider with a setup screen such as that shown in FIG. 5. The inputting of information by the rider to build the rider's workout is now described with reference to FIGS. 11A-F, which represent successive steps of a setup screen such as that shown by display 200 as in FIG. 5.

Figure 11A:
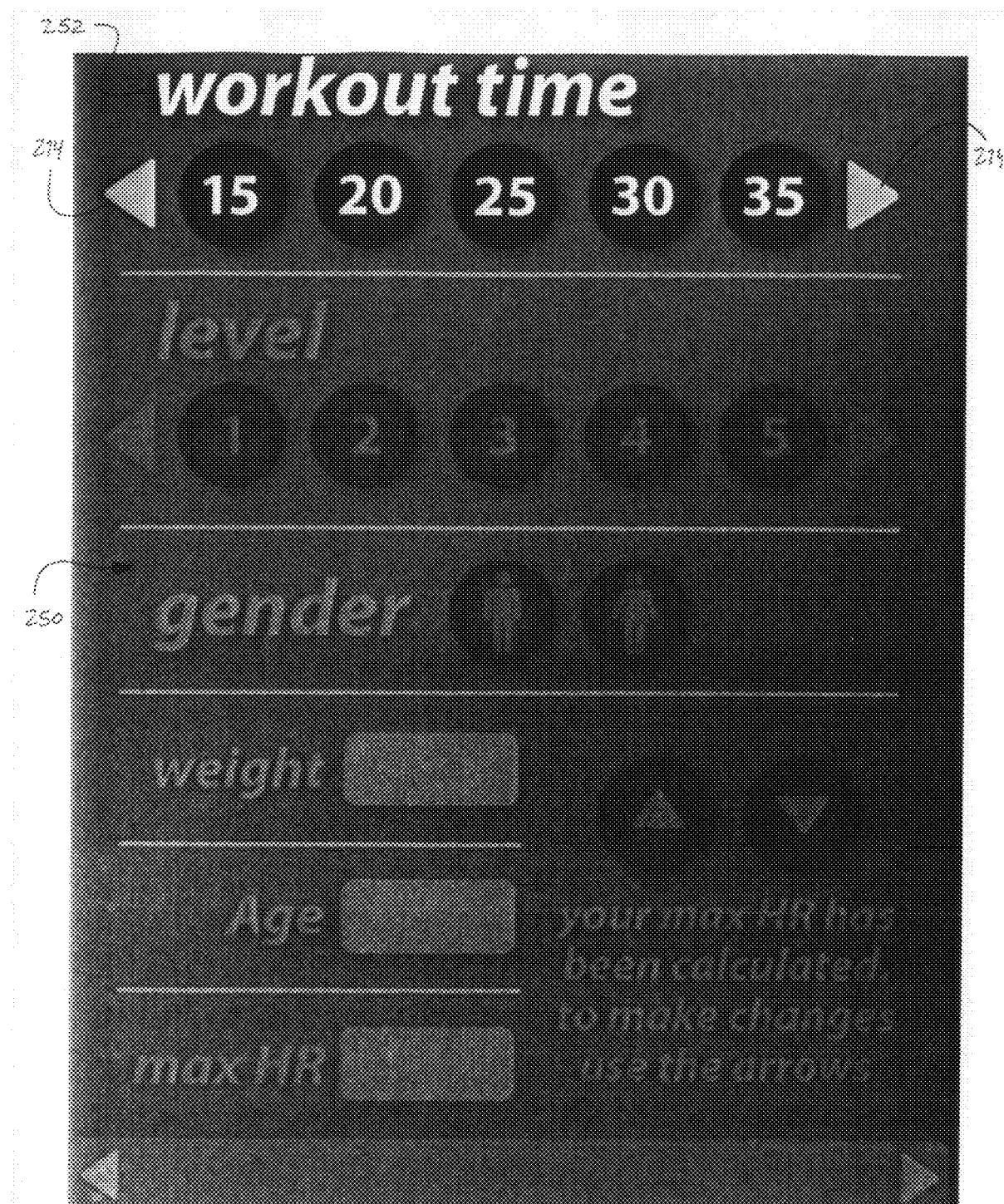
FIGS. 11A-F show different stages of a set up screen of a display.

The rider may input information starting with the workout time 252 as in FIG. 11A. To direct the rider's attention to this input parameter, the workout time designation may be illuminated. As shown, the workout times 252 available may be in five minute increments, though different increments may be used. If the rider desires a shorter or longer workout, he or she may use the arrows 254 to scroll left or right to a desired workout time.

Figure 11B:
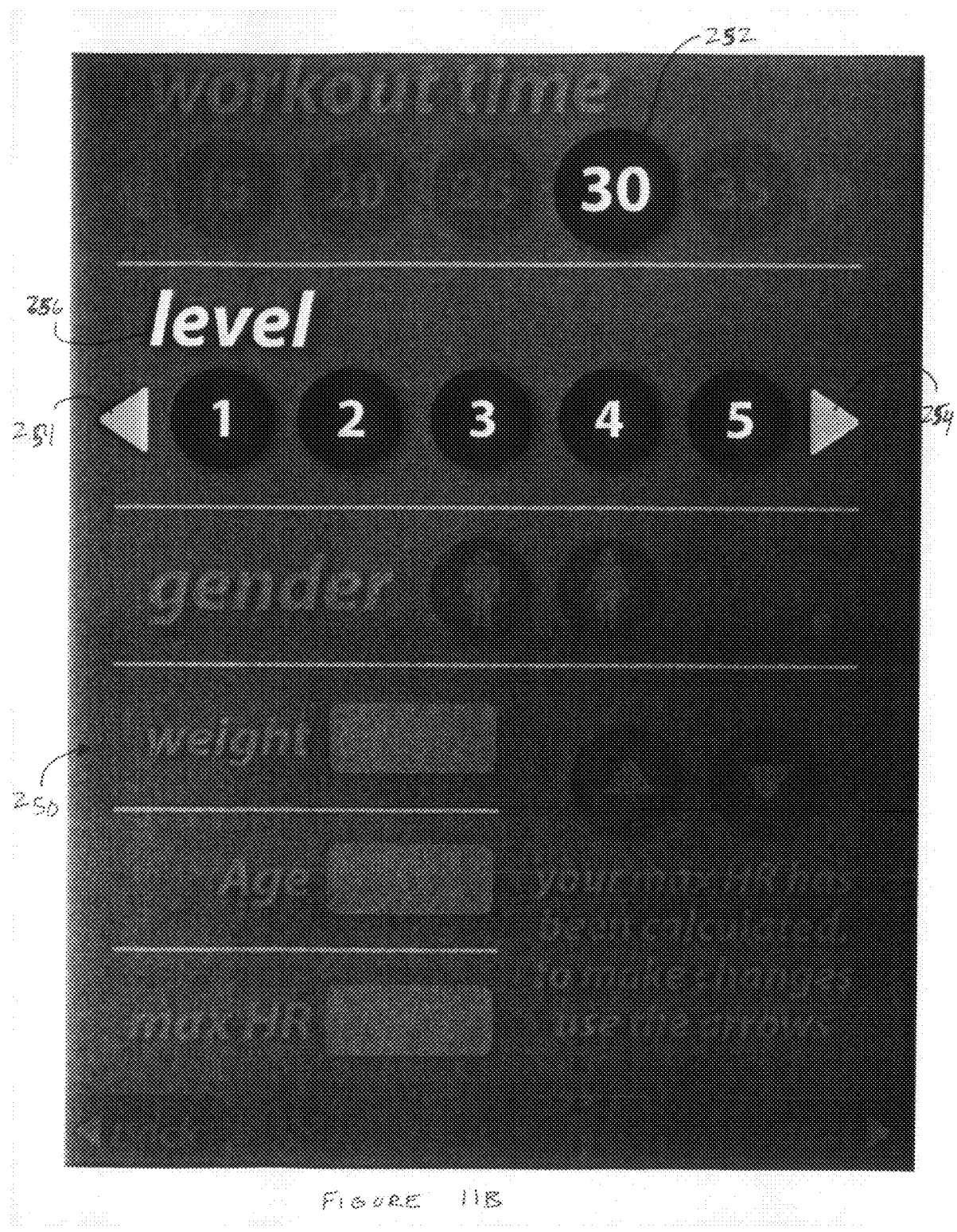

When the workout time 252 has been chosen, the next input parameter, e.g., level 256, may be illuminated to focus the rider's attention thereto as shown in FIG. 11B. Intensity level 256 may be presented in integer increments. If the rider desires an intensity level that is not displayed on screen 250, the rider may use arrows 254 to scroll to the desired level 256.

Figure 11C:

When the intensity level 256 has been chosen, the next input parameter, e.g., gender 258, may be illuminated to focus the rider's attention thereto as shown in FIG. 11C.

When gender 258 is input, the weight 242 field may become illuminated and a portion of screen 250 may display a numerical key pad 244 as shown in FIG. 11C. The rider may input his or her weight. After pressing the numerals for his or her weight, the rider may press the enter button 245.

Figure 11D:

As shown in FIG. 11D, the rider may then enter his or her age 246 using numerical keypad 244 and pressing the enter button 245 while the age 284 field is illuminated.

Figure 11E:
Figure 11F:
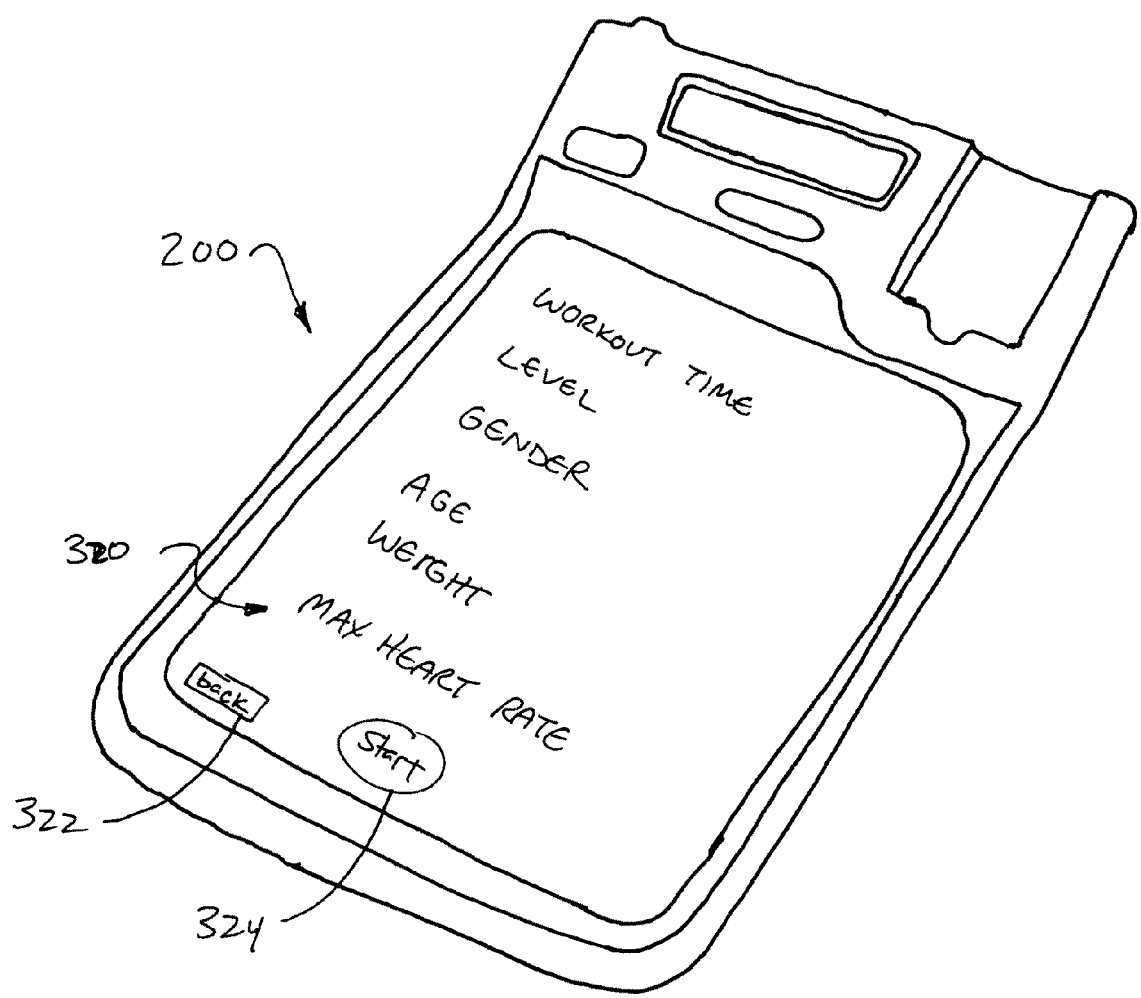

At this point, the computer may calculate the max heart rate 247 as shown in FIG. 11E. As discussed below, the max heart rate 247 may be used to help guide the rider through the workout. But if the rider desires to increase or decrease the max heart rate 247, he or she may do so with arrows 274.

It should be noted that the present invention is not limited to input of the types of information described above. Other information may also be input. When the foregoing parameters and/or other appropriate parameters have been inputted, the rider may hit the next button 248 in FIG. 11F which provides a summary screen 310. If the rider wants to change any of the information in screen 310, he or she may hit the back button 322. Otherwise, the rider may hit the start button 324 and begin the workout.

Figure 12A:
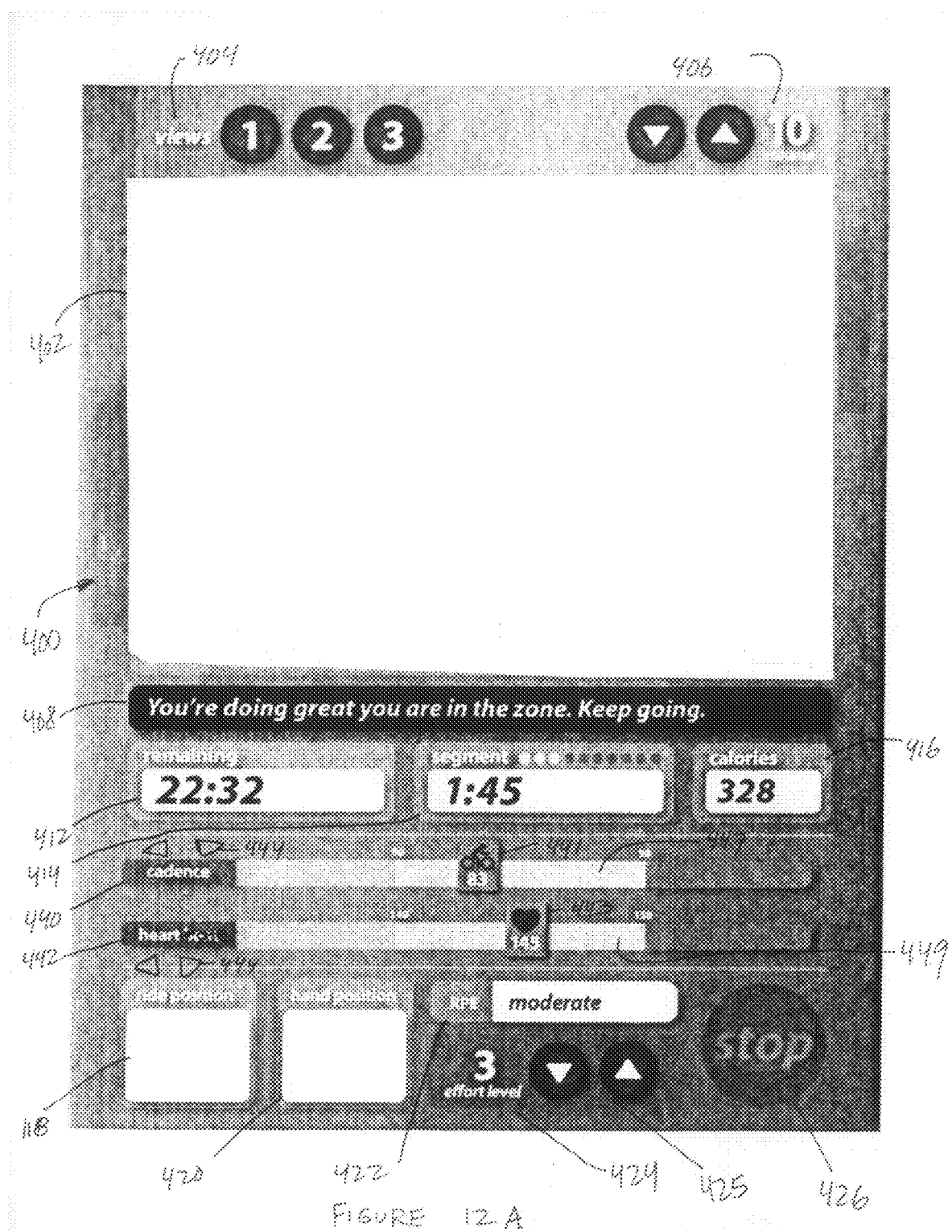
FIG. 12A shows a screen of a display.
Figure 12B:
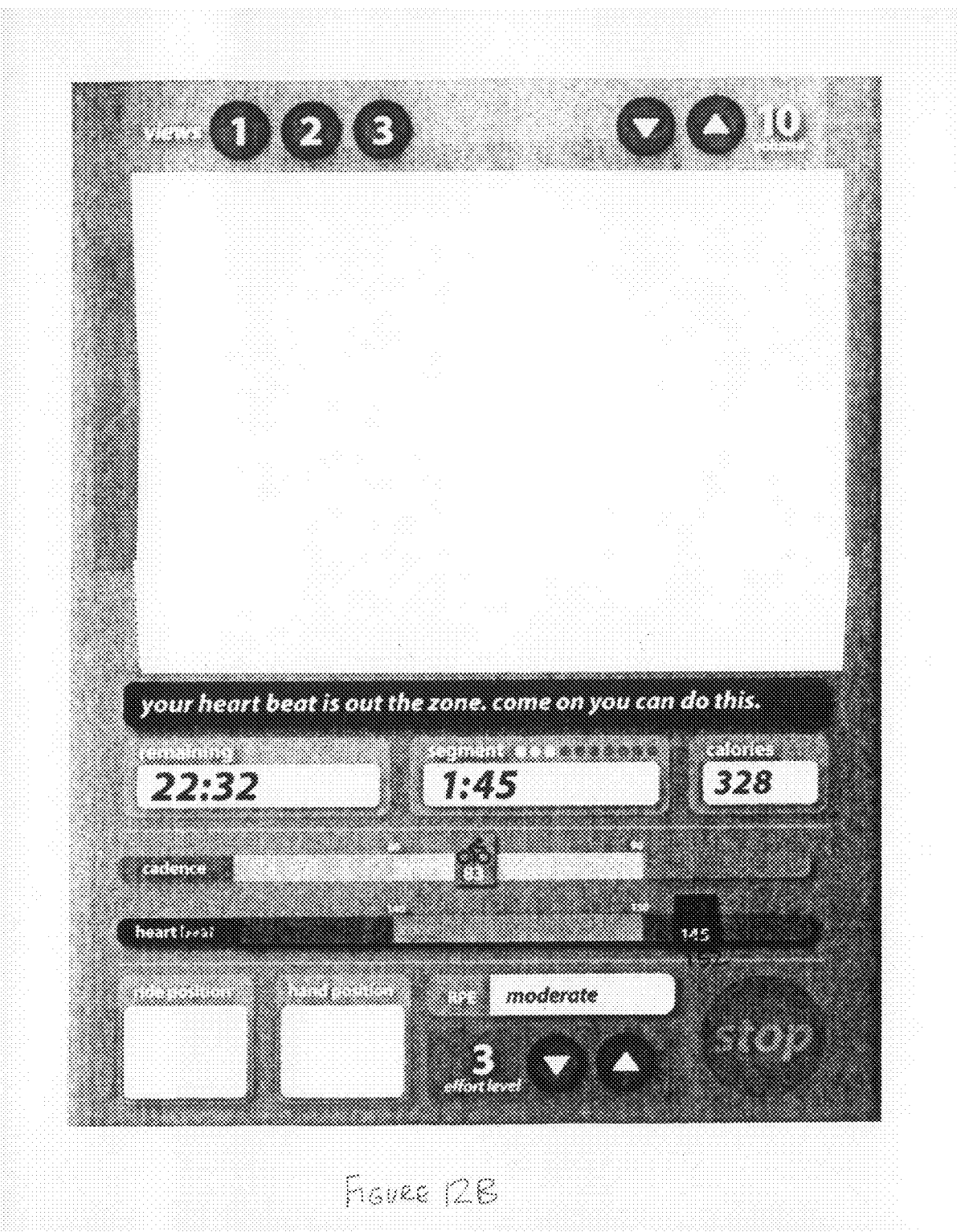
FIG. 12B shows a screen of a display.

As shown in FIG. 12A, display 200 may show screen 400 for the rider's workout. As discussed later in more detail, the screen in FIG. 12A may be displayed when the rider's heart beat is in the appropriate range. FIG. 12B, which is similar to the screen of FIG. 12A but with certain items highlighted such as the heartbeat field, may be displayed when the rider's heart rate is too low or too high. The highlighted nature is intended to bring the rider's attention to the heartbeat. Once the heart beat is in the intended range, the screen of FIG. 12A may again be displayed.

A portion of screen 400 may comprise a video screen 402. The video content may comprise an instructor leading the rider through the exercise, a road or trail that simulates the riding conditions the rider is undergoing or other video like the rider's favorite TV show. The content displayed on video screen 402 may be changed by the rider by pressing any of the view buttons 404. At the beginning of the workout, screen 402 may display a general graphic of the hear rate profile with text stating the goals of the program.

Throughout the workout, different instructions in riding positions and hand positions are provided at appropriate times during the workout The rider may control the volume of the instructions, music or other audio content by volume buttons 406. The display may have an assortment of audio content that the rider may choose to listen to while exercising. Alternatively, the audio content may be programmed into display 200 to automatically accompany the type of exercise chosen by the rider. Alternatively, the rider may insert his or her iPod or other similar device in cavity 220 of display 200. In this embodiment, cavity 220 may serve as a docking station and the iPod may provide the video and/or audio content.

An instruction bar or message window 408 may appear below video screen 402 and may display instructions to the rider such as for the rider to change riding or hand positions, to gradually add resistance to increase heart rate, decrease resistance to lower heart rate, etc. General messages and encouraging messages may also be displayed by window 408. Along with the written instruction in bar 408, the spoken instructions may also be provided through speaker 222 of display 200.

Screen 400 preferably includes a ride position field 418 and a hand position field 420 which may display the posture and hand position that the rider should assume during that part of the workout. The ride position field 418 may show the rider in a sitting, standing or other position as described previously. The hand position field 420 may show different points on the handlebars where the rider's hands should be placed as described previously.

Screen 400 may also include a rate of perceived exertion field (RPE) field 422 which may display different levels of difficulty such as easy, moderate, hard or very hard that may be associated with heart rate targets with particular segments of the workout. For each heart rate target, there may be a corresponding RPE. When a rider is not wearing a heart rate strap or other device to monitor heart rate, the rider can observe the RPE to gauge their intensity.

Screen 400 may also include an effort level field 424. The level of effort may be increased or decreased by arrows 425. By adjusting the effort level, the rider's heart rate and/or cadence targets may go up or down. When the effort level is increased or decreased, the rider may be instructed to increase or decrease the resistance. In an embodiment of the invention, screen 400 may include a button that will transmit a signal to the resistance adjustment device to vary the resistance provided thereby.

Figure 13:
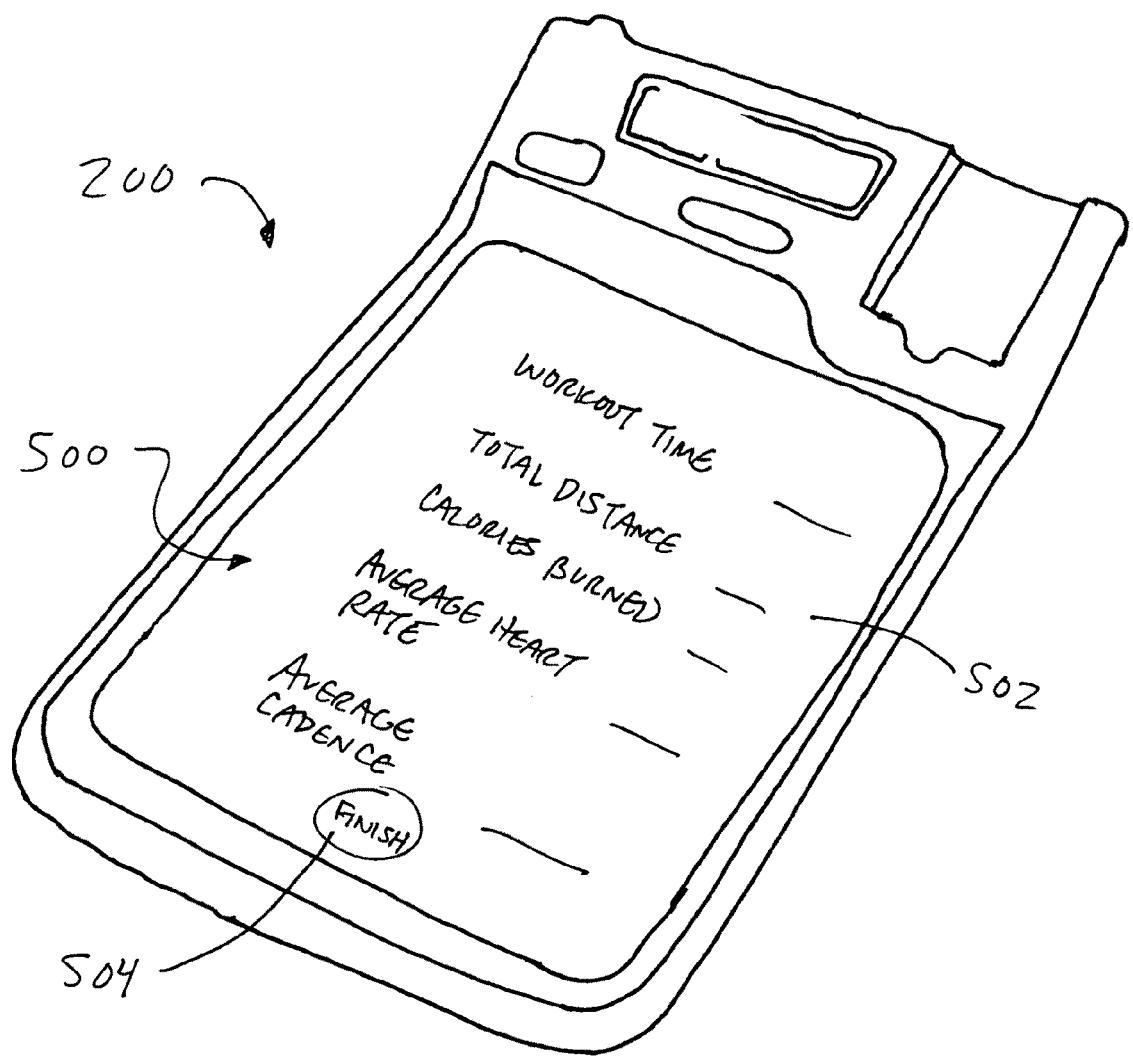
FIG. 13 shows a screen of a display.

Screen 400 preferably includes a stop/pause button 426 so that the rider may stop and pause the workout if he or she needs to dismount the bike. If button 426 is pressed, a screen may pop up asking the rider if he or she wants to end the workout. If the rider presses yes, the workout ends and screen 200 displays a workout summary screen that provides information 502 such as workout time, total distance, calories burned, average heart rate and average cadence as shown in FIG. 13. The rider may then press the finish button 504 and the screen may revert to the screen shown in FIG. 7. Referring back to the rider being prompted whether he or she wants to end the workout, If the rider presses no, the rider is taken back to the workout to resume where he or she left off.

Preferably, the workout will have different segments that make up the overall workout time. For example, one segment may simulate climbing a hill where the resistance is adjusted up, a standing riding position is assumed and the cadence is decreased. Another segment may simulate a flat section of road where the resistance is adjusted down, the rider is instructed to sit and the cadence is increased.

The overall time remaining may be displayed in time field 412, and the time remaining in a particular segment may appear in segment field 414. A different riding position, hand position and/or resistance adjustment setting may be associated with each segment. And as one segment ends, the instruction bar 408 may alert the rider that in a certain amount of time, the rider should change his or her riding position, hand position and/or resistance setting. When the segment changes the ride position in field 418 and the hand position in field 420 may change appropriately. There may also be warm up and cool down segments.

Instruction bar 408 may also provide messages encouraging the rider through the workout, such as "you're doing great; keep going." These messages may also be audibly spoken through the speaker 222 in display 200.

Workout screen 400 may also include a calories field 416 which may display the number of calories burned to that point in the workout. The number of calories burned preferably depends on the information inputted by the rider. In another embodiment, it is not dependent on personalized information of the rider.

Screen 400 also preferably include a cadence bar 440 and heart rate bar 442. Cadence bar may include cadence icon 441 which displays the actual cadence in revolutions per minute that the rider is pedaling at. To this end, the computer in display 200 may be coupled to the flywheel to determine RPMs. The actual cadence may be determined by taking the gear ratio into account. Heart rate bar 442 may include a heart icon 443 that displays the rider's actual heart rate in beats per minute. Both the cadence bar 440 and heart rate bar 442 may include arrows 444.

Cadence bar 440 may display a target zone 447, e.g., between 80 and 90 revolutions per minute as shown in FIG. 12A, in which the rider should try to remain. The cadence zone 447 may change according to the segment of the workout. For example, if the segment involves climbing a hill, the cadence zone will be lower. While if the segment involves a flat sprint, the cadence will be higher.

The zone 447 part of the cadence bar 440 may be green to reflect that it is the desired zone. The parts of the cadence bar 440 to the right or left of zone 447 may be red to reflect that the rider should try to avoid cadences higher than 90 RPMs, or cadences lower than 80 RPMs. If the rider's cadence falls above or below zone 447, the cadence bar 440 may turn red or be highlighted (similar to the highlighting of heart rate bar 442 in FIG. 12B) to bring the rider's attention that he or she should increase or decrease cadence. The instruction bar 408 may provide instructions to that effect, and an audio instruction may also be provided.

Heart rate bar 442 may also display the rider's actual heart rate though an icon. The actual heart rate may be supplied by heart rate monitor worn by the rider being connected to the display 200. Display 200 may preferably acquire and interpret telemetric heart rate signals from coded and non-coded heart rate straps. Heart rate bar may also display a target zone 449, e.g., between 140 and 150 beats per minute, in which the rider should try to remain. The heart rate zone 449 may be dependent on the information such as age, weight and gender input by the rider before the workout. The zone 449 part of the heart rate bar 442 may be green to reflect that it is the desired zone. The parts of the heart rate bar 442 the right or left of zone 449 may be red to reflect that the rider should try to avoid heart beat rates higher than 150 beats per minute, or lower than 140 beats per minute. If the rider's heart rate falls above or below zone 449, the heart rate bar 442 may turn red or be highlighted as shown in FIG. 12B to bring the rider's attention that he or she should increase or decrease heart rate.

The instruction bar 408 may provide instructions to lower the heart rate, e.g., decrease resistance if the rider's cadence is in the zone or lower cadence is the rider's cadence exceeds the zone. An audio instruction may also be provided.

It should be noted that the layout of workout screen 400 may vary without departing from the scope of the current invention. For example, cadence bar 440 and heart rate bar 442 may resemble a speedometer having a needle, wherein cadence RPMs and heart beats per minute are laid out on a dial similar to miles per hour are on a speedometer. Cadence zone 441 and heart rate zone 443 may also be laid out on the dial. The actual cadence or heart rate would be represented by the needle as are miles per hour represented in a speedometer. And if the cadence or heart rate falls outside the respective zones, the dial could turn red or be highlighted.

Once the workout is done, screen 400 will so indicate. At that point, display 200 may display the workout summary screen 500 of FIG. 13. At that point, the rider may press the finish button 504 and return to screen 270 of FIG. 7.

As noted above, another of the options on screen 270 is the SPINNING class videos option 272. If the rider chooses this option 272 screen 250 may display the screen 290 of FIG. 9. As shown, several different workout options may be shown such as split terrain 292, interval challenge 294 and riding strong or strength 296. The user may hit the information button 297 to obtain a textual description of what the workout entails. As with the screen 300 of FIG. 10, the invention is not limited to the workout examples identified above. To that end, it is preferred that the rider may scroll across screen 290 to other workout options.

Figure 9:
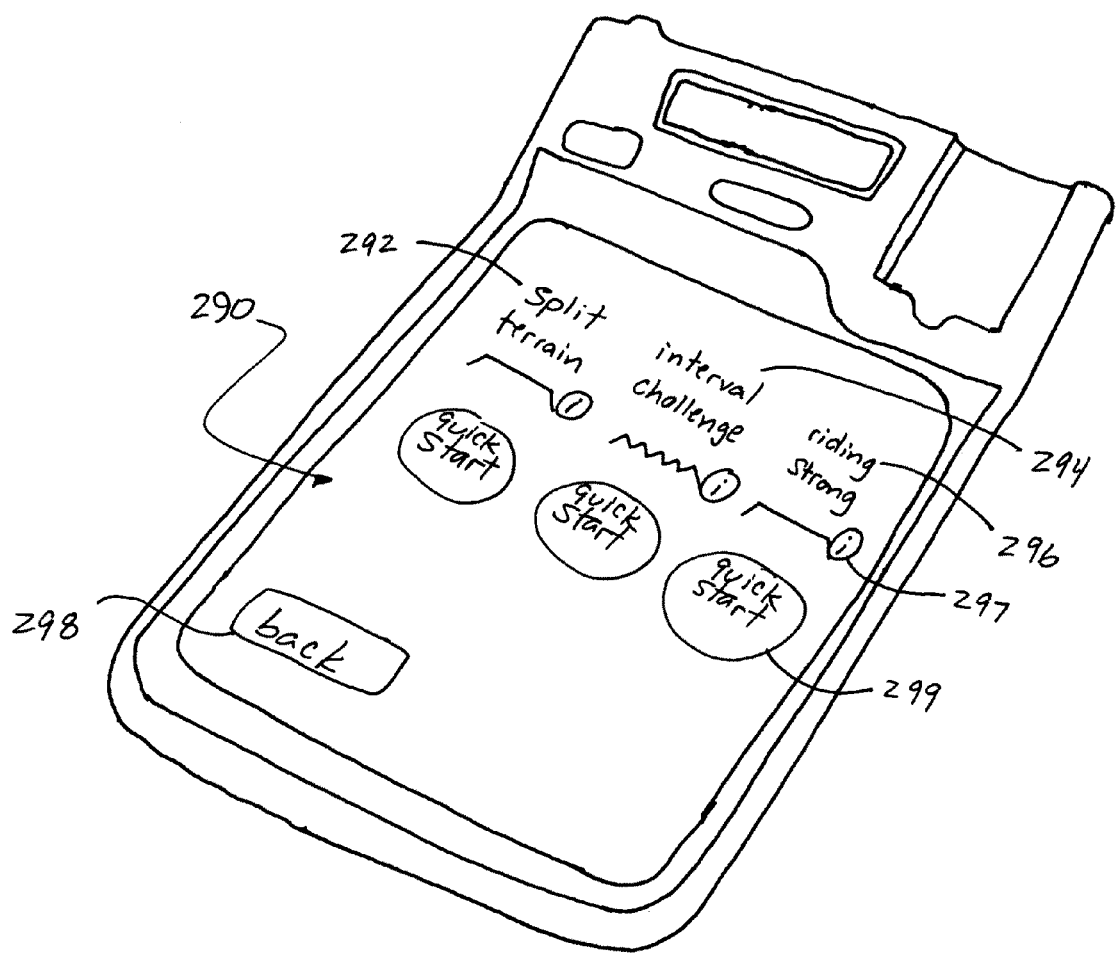
FIG. 9 shows a screen of a display.

As shown in FIG. 9, each workout option may include a quick start button 299. By hitting this button, the rider is preferably taken to workout screen 400 without having to go through all the set up screens 250 of FIGS. 11A-F. In essence, if the rider selects option 272 he or she may quickly start the workout. In this embodiment, the workout may proceed irrespective of the rider's personal information, e.g., weight, age, etc.

In an embodiment of the current invention, a personalized workout may be stored on a memory device such as a memory stick. Preferably, the memory stick may be plugged into display 200, e.g., plugged into a USB port in the console of display 200. The information on the memory stick may be downloaded thereto from the rider's personal trainer, or may be downloaded from the internet. In any event, it is preferred that the information on the memory stick may be easily downloaded to the computer in display 200. The information downloaded from the memory stick to the computer in display 200 may also include personal information of the rider such as weight, age, etc. As such, the downloading may perform the programming such as that performed through the setup screens described above. In this manner, the computer is preferably programmed quickly, and the rider may begin his or her workout.

Figure 14:
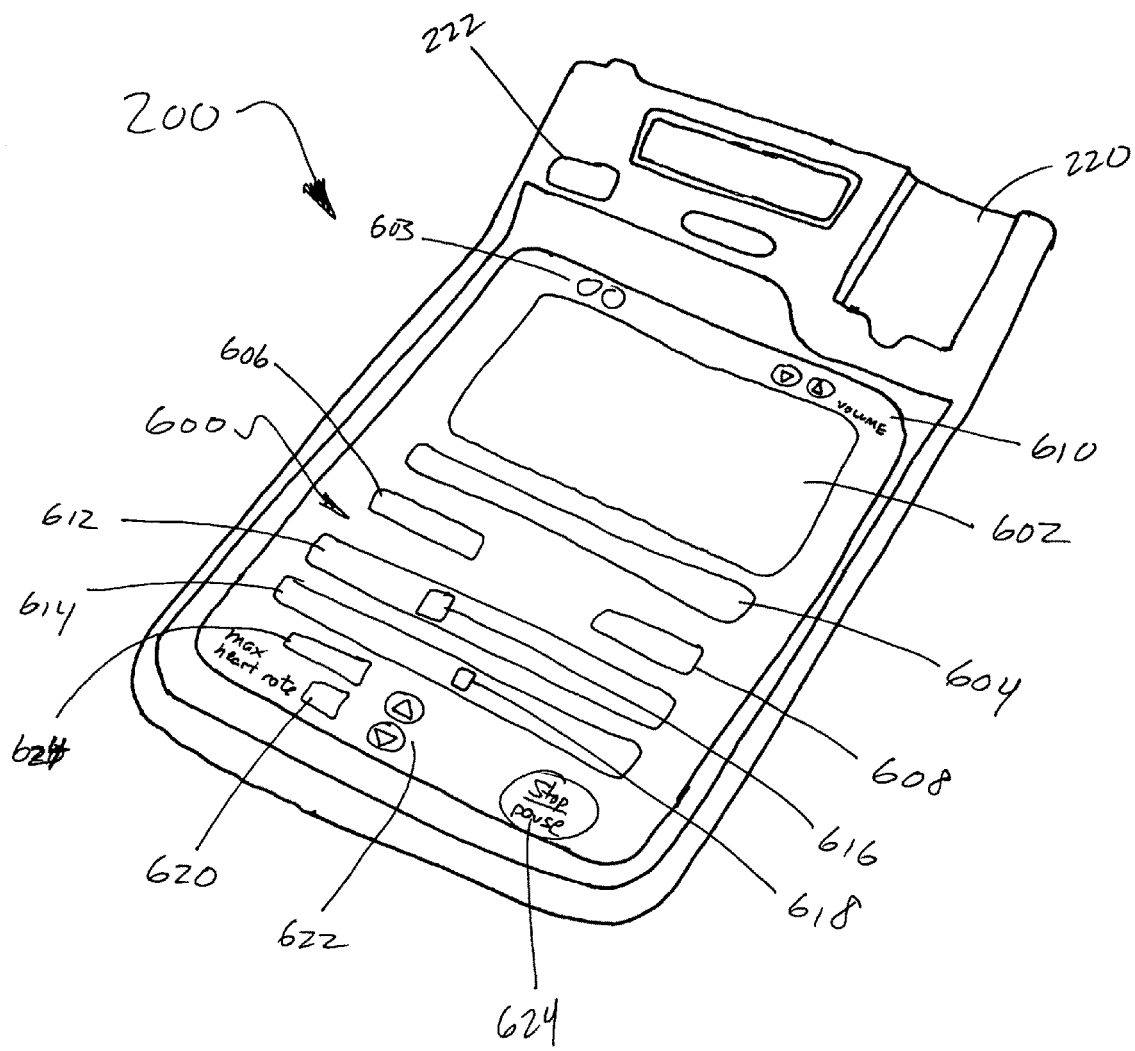
FIG. 14 shows a screen of a display.

The ride to my media option 276 on screen 270 is now further described. If this option is chosen, screen 600 may appear as shown in FIG. 14. This option may not be associated with any exercise that may be preprogrammed into display 200 such as those described above. Rather, screen 600 may simply display overall information as follows.

Screen 600 may include video display 602 that may display a video chosen by the rider by using video buttons 603. The video may be a favorite TV show, video of a road simulating a bike ride, or other video content. If the rider desires music or some other audio content, the volume may be controlled by buttons 610. Screen 600 may include a message bar 604 that may provide encouragement to the rider or other information. Time field 606 may indicate how long the rider has been riding. Calorie field 608 may indicate how many calories the rider has burned so far. This may be generalized or average calorie burn rate information and need not be dependent on a particular rider's personal information.

Screen 600 may also include cadence bar 612 with a cadence icon 616, and heart rate bar 614 with a heart rate icon 618. When choosing the ride to my media option 276, the rider may input a max heart rate 620 by using buttons 622. Field 624 may then display the percentage of max heart rate at which the rider's heart is beating. Screen 600 may also include a stop/pause button 624 that may work as described above.

As noted earlier with FIG. 5, display 200 may include fan 216 that may be controlled by fan control 214. The default of fan 216 may be set at a non running state. The fan control 214 may comprise a button which when pressed will set the fan to 100% of its running capacity. If fan control button 214 is pressed again, fan 216 may adjust to some other percentage of running capacity. And if fan control button 214 is pressed again, fan 216 may turn off.

Figure 15:
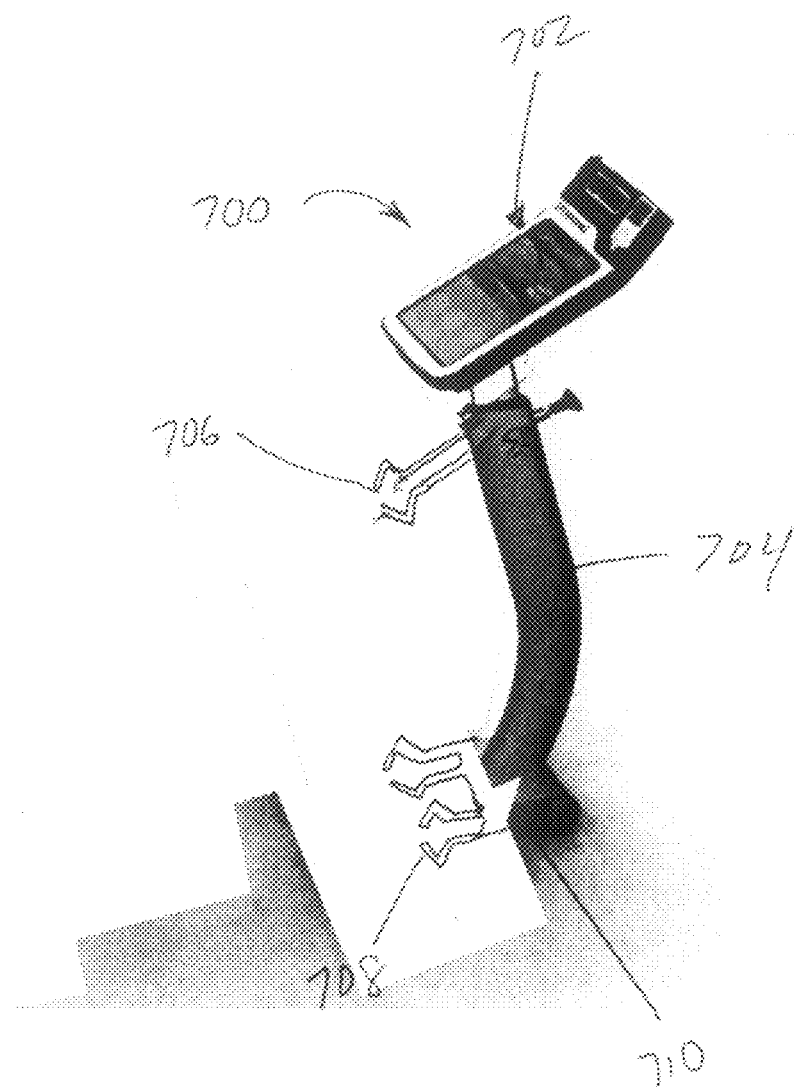
FIG. 15 shows a display module.

Another aspect of the invention relating to a display module 700 is now further described with reference to FIG. 15. As shown, display module 700 may exist separate and apart from an exercise bike. Display module 700 may include display 200 similar to that described above. Display module may also generally have the same configuration as display stand 770 described in FIG. 4.

Display module 700 may preferably be attached to an exercise bike thereby converting the bike to a programmable bike similar to that of the current invention. As shown, display module 700 may include an upper clamping member 706 and lower clamping members 708 to attach display module 700 to a bike or other piece of exercise equipment. Different means to attach display module 700 to a bike may be used, such as clamps or other suitable means such as a vice grip type arrangement, nut and bolt, etc. The type of attaching means and the configuration thereof may be altered to suit a particular brand of bike that the display module 700 is intended for.

Alternatively, display module 700 may comprise a stand alone device that is not attached to a bike. In this embodiment, the base 710 of display module 700 is preferably broad enough so that it may remain upright as the rider presses various buttons on display 200.

Bike 10 of the current invention provides many benefits over other stationary bikes that may include some amount of computer guidance. Many such stationary bikes simply do not offer the type of workout that the current bike offers. For example, the LIFECYCLE type bike does not have the geometry to permit alternating standing and sitting in a smooth manner. In contrast, bike 10 of the current invention is intended for alternating standing and sitting and thus allows different riding positions. This in turn burns more calories and provides for a total body workout by using different muscle groups. For example, the standing position allows core abdominal muscles to be used. This is not achieved by the LIFECYCLE type bike.

The LIFECYCLE type bike does not provide instructions regarding various riding and handlebar positions that allow for a workout that involves a bike ride that simulates an outdoor ride with flats, hills and other conditions. Bike 10 of the current invention provides these type of instructions. The LIFECYCLE type bike also does not offer the variety of personalized rides that bike 10 of the current invention offers.

The current invention also provides an advance over indoor cycling bikes that may be located on the health club floor for random use without an instructor. These other type of indoor cycling bikes may pose a safety threat, especially when in a fixed gear configuration. Bike 10 of the current invention may provide instructions regarding a cadence limit, or other variables to reduce or avoid this risk. The instructions may also take the rider's health into account. Accordingly, bike 10 overcomes some of the risks associated with random, non-instructed use of indoor cycling bikes that are typically used in a group class led by an instructor.

Although certain presently preferred embodiments of the invention have been described herein, it will be apparent to those skilled in the art to which the invention pertains that variations and modifications of the described embodiments may be made without departing from the spirit and scope of the invention.

What is claimed is:

1. A programmable stationary exercise bike, comprising:
a bike;
a resistance adjustment mechanism coupled to the bike for a rider to adjust a pedaling resistance of the bike during a workout; and
a touch screen display including a computer mounted to the bike, wherein the display provides a workout based on personalized information of the rider that is programmed into the computer through the touch screens display, wherein the workout proceeds by measuring the rider's cadence and heart rate, and wherein a plurality of instructions in different media are provided to the rider to lead the rider through the workout, the instructions including a video of an instructor providing visual and audio instructions leading the rider through the workout, and textual instructions or graphical instructions that are coordinated with the instructor video for at least part of the workout, to the rider to vary the rider's cadence or adjust the pedaling resistance of the bike so that the rider's cadence and heart rate fall within target zones based on the rider's personalized information.

2. The exercise bike of claim 1, wherein the bike further comprises handlebars coupled to the bike and wherein the video of the instructor provides instructions to the rider to vary riding positions by alternating between sitting and standing and by varying hand positions on the handlebars in order to maintain the rider's heart rate within the target zones.

3. The exercise bike of claim 2, wherein the instructions to vary riding positions are provided to the rider in the form of static images of a rider in different riding positions.

4. The exercise bike of claim 1, wherein the personalized information input by the rider includes a heart rate profile selected from a plurality of heart rate profiles.

5. The exercise bike of claim 4, wherein the heart rate profile selected by the rider is modified by the computer based on the personalized information input by the rider through the touch screen display.

6. The exercise bike of claim 5, wherein the personalized information includes one or more of age, gender, and weight.

7. The exercise bike of claim 6, wherein the personalized information includes a level of exertion and duration of time for the workout.

8. The exercise bike of claim 5, wherein the rider's actual heart rate is displayed on the touch screen display near to the heart rate profile selected by the rider.

9. The exercise bike of claim 1, wherein the rider's cadence is displayed on the touch screen display.

10. The exercise bike of claim 9, wherein the rider's cadence is displayed by a cadence indicator on a cadence bar that also indicates a target cadence range.

11. The exercise bike of claim 10, wherein the cadence indicator changes color when the cadence of the rider moves into or out of the target cadence range.

12. The exercise bike of claim 1, wherein the rider's heart rate is displayed on the touch screen display.

13. The exercise bike of claim 12, wherein the rider's heart rate is displayed by a heart rate indicator on a heart rate bar that also indicates a target heart rate range.

14. The exercise bike of claim 13, wherein the heart rate indicator changes color when the rider's heart rate moves into or out of the target heart rate range.

15. The exercise bike of claim 1, wherein the instructions are provided to the rider by text located on the touch screen display.

16. The exercise bike of claim 1, wherein the display further provides a workout option based on personal media displayed on the touch screen display.

17. The exercise bike of claim 16, wherein the personal media originates from an iPod, phone, television signal, digital music player, or universal serial bus flash memory device.

18. The exercise bike of claim 17, wherein the display further provides a workout option based on data downloaded from the internet.

19. The exercise bike of claim 17, wherein the touch screen display provides a setup video for the bike.

20. The exercise bike of claim 19, wherein the touch screen display provides an introductory video demonstrating capabilities of the bike.

21. The exercise bike of claim 4, wherein the plurality of heart rate profiles includes endurance, interval, and strength.

22. The exercise bike of claim 1, wherein the display further provides a workout based on a heart rate profile generated by the computer and based on personalized information of the rider that is input into the computer through the touch screen display, wherein the rider's actual heart rate is displayed on the touch screen display near to the heart rate profile generated by the computer.

23. A programmable stationary exercise bike, comprising:
a bike with handlebars coupled to the bike;
a resistance adjustment mechanism coupled to the bike for a rider to adjust the pedaling resistance of the bike during a workout; and
a touch screen display including a computer mounted to the bike, wherein the display provides a bike setup video, an introductory video demonstrating operation of the bike, and workout options, including:
- a workout based on personal media displayed on the touch screen display wherein the personal media can originate from an iPod, phone, television signal, digital music player, or universal serial bus flash memory device; and
- a workout based on a heart rate profile, wherein a video of an instructor providing visual and audio instructions leading the rider through the workout, and textual instructions or graphical instructions that are coordinated with the instructor video for at least part of the workout are provided to the rider to vary a rider cadence, to adjust the pedaling resistance of the bike, and to vary riding positions by alternating between sitting and standing positions and by varying hand positions on the handlebars in order to maintain a rider's heart rate within a target zone, wherein the heart rate profile, the video of the instructor, and the two or more of the textual, graphical or audio instructions provided to the rider are generated by the computer based on input received from the rider through the touch screen display.

24. The exercise bike of claim 23, wherein the touch screen display provides a rider's cadence on a cadence bar and a rider's heart rate on a heart rate bar and icons and text that provide instructions to vary a riding position by alternating between sitting and standing positions and by varying hand positions.

25. The exercise bike of claim 23, wherein the workout options include a workout based on a heart rate profile generated from the input received from the rider, wherein the rider's actual heart rate is displayed on the touch screen display next to the heart rate profile generated by the computer.

26. The exercise bike of claim 23, wherein the input received from the rider includes selecting a heart rate profile from one of endurance, interval, or strength.

* * * * *